(12) United States Patent
Shoemaker et al.

(10) Patent No.: US 6,713,257 B2
(45) Date of Patent: Mar. 30, 2004

(54) GENE DISCOVERY USING MICROARRAYS

(75) Inventors: Daniel D. Shoemaker, Bothell, WA (US); Stewart Scherer, Moraga, CA (US); Steven J. Altschuler, Redmond, WA (US); Lani F. Wu, Redmond, WA (US); Christopher D. Armour, Kirkland, WA (US)

(73) Assignee: Rosetta Inpharmatics LLC, Kirkland, WA (US)

( * ) Notice: Subject to any disclaimer, the term of this patent is extended or adjusted under 35 U.S.C. 154(b) by 0 days.

(21) Appl. No.: 09/781,814

(22) Filed: Feb. 12, 2001

(65) Prior Publication Data

US 2002/0045169 A1 Apr. 18, 2002

Related U.S. Application Data

(60) Provisional application No. 60/227,966, filed on Aug. 25, 2000, and provisional application No. 60/227,902, filed on Aug. 25, 2000.

(51) Int. Cl.$^7$ .......................... C12Q 1/68; C07H 21/02; C07H 21/04; G06F 19/00

(52) U.S. Cl. .......................... 435/6; 536/23.1; 536/24.3; 702/19; 702/20

(58) Field of Search .......................... 435/6; 536/23.1, 536/24.3; 702/19, 20

(56) References Cited

U.S. PATENT DOCUMENTS

| | | | |
|---|---|---|---|
| 5,445,934 A | 8/1995 | Fodor et al. |
| 5,510,270 A | 4/1996 | Fodor et al. |
| 5,539,083 A | 7/1996 | Cook et al. |
| 5,545,522 A | 8/1996 | Van Gelder et al. |
| 5,552,270 A | 9/1996 | Khrapko et al. |
| 5,556,749 A | 9/1996 | Mitsuhashi et al. |
| 5,556,752 A | 9/1996 | Lockhart et al. |
| 5,569,588 A | 10/1996 | Ashby et al. |
| 5,578,832 A | 11/1996 | Trulson et al. |
| 5,631,134 A | 5/1997 | Cantor |
| 5,716,785 A | 2/1998 | Van Gelder et al. |
| 5,723,320 A | 3/1998 | Dehlinger |
| 5,744,305 A | 4/1998 | Fodor et al. |
| 5,837,832 A | 11/1998 | Chee et al. |

(List continued on next page.)

FOREIGN PATENT DOCUMENTS

| | | |
|---|---|---|
| WO | WO 98/12354 | 3/1998 |
| WO | WO 98/38329 | 9/1998 |
| WO | WO 99/09164 | 2/1999 |
| WO | WO 99/19357 | 4/1999 |
| WO | WO 99/28506 | 6/1999 |
| WO | WO 99/34004 | 7/1999 |
| WO | WO 99/43848 | 9/1999 |
| WO | WO 99/57315 | 11/1999 |
| WO | WO 99/57322 | 11/1999 |
| WO | WO 99/58708 | 11/1999 |

(List continued on next page.)

OTHER PUBLICATIONS

Adams et al., 1991, "Complementary DNA sequencing: expressed sequence tags and human genome project," Science 252(5013):1651–6.

Ahrendt, 1999, "Rapid p53 sequence analysis in primary lung cancer using an oligonucleotide probe array," Proc. Natl. Acad. Sci. U. S. A. 96(13):7382–7.

(List continued on next page.)

*Primary Examiner*—Kenneth R. Horlick
*Assistant Examiner*—Teresa Strzelecka
(74) *Attorney, Agent, or Firm*—Pennie & Edmonds LLP

(57) ABSTRACT

The invention relates to methods and systems (e.g., computer systems and computer program products) for identifying and characterizing genes using microarrays. In particular, the invention provides for improved, robust methods for detecting genes through the use of microarrays to analyze the expression state of the genome. Genes which are expressed can be mapped to their respective positions in the genome, and the structure of such genes can be determined.

41 Claims, 19 Drawing Sheets

U.S. PATENT DOCUMENTS

| | | |
|---|---|---|
| 5,843,767 A | 12/1998 | Beattie |
| 5,856,103 A | 1/1999 | Gray et al. |
| 5,891,636 A | 4/1999 | Van Gelder et al. |
| 5,935,793 A | 8/1999 | Wong |
| 5,965,352 A | 10/1999 | Stoughton et al. |
| 5,972,619 A | 10/1999 | Drmanac et al. |
| 5,981,176 A | 11/1999 | Wallace |
| 5,981,190 A | 11/1999 | Israel |
| 6,007,987 A | 12/1999 | Cantor et al. |
| 6,027,880 A | 2/2000 | Cronin et al. |
| 6,028,189 A | 2/2000 | Blanchard |
| 6,040,138 A | 3/2000 | Lockhart et al. |
| 6,045,996 A | 4/2000 | Cronin et al. |
| 6,057,111 A | 5/2000 | Deiss et al. |
| 6,110,676 A | 8/2000 | Coull et al. |
| 6,132,969 A | 10/2000 | Stoughton et al. |
| 6,146,830 A | 11/2000 | Friend et al. |
| 6,156,502 A | 12/2000 | Beattie |
| 6,203,987 B1 | 3/2001 | Friend et al. |
| 6,218,122 B1 | 4/2001 | Friend et al. |
| 6,222,093 B1 | 4/2001 | Marton et al. |
| 6,271,002 B1 | 8/2001 | Linsley et al. |
| 6,324,479 B1 | 11/2001 | Friend et al. |
| 2002/0048763 A1 | 4/2002 | Penn et al. |
| 2002/0081590 A1 | 6/2002 | Penn et al. |

FOREIGN PATENT DOCUMENTS

| | | |
|---|---|---|
| WO | WO 99/59037 | 11/1999 |
| WO | WO 99/66067 | 12/1999 |
| WO | WO 00/05414 | 2/2000 |
| WO | WO 00/24936 | 5/2000 |
| WO | WO 00/34523 | 6/2000 |
| WO | WO 00/39336 | 7/2000 |
| WO | WO 00/39339 | 7/2000 |
| WO | WO 00/43942 | 7/2000 |
| WO | WO 00/47766 | 8/2000 |
| WO | WO 00/47767 | 8/2000 |
| WO | WO 00/53811 | 9/2000 |
| WO | WO 00/56929 | 9/2000 |
| WO | WO 00/65088 | 11/2000 |
| WO | WO 00/77261 | 12/2000 |
| WO | WO 00/79006 | 12/2000 |
| WO | WO 01/05935 | 1/2001 |
| WO | WO 01/57251 | 8/2001 |
| WO | WO 01/57252 | 8/2001 |
| WO | WO 01/81632 | 11/2001 |

OTHER PUBLICATIONS

Alon, 1999, "Broad patterns of gene expression revealed by clustering analysis of tumor and normal colon tissues probed by oligonucleotide arrays," Proc. Natl. Acad. Sci. U. S. A. 96(12):6745–50.

Altschul et al., 1990, "Basic local alignment search tool," J. Mol. Biol. 215(3):403–10.

Bell et al., 1998, "Influence of intron length on alternative splicing of CD44," Mol. Cell. Biol. 18:5930–5941.

Blanchard and Friend, 1999, "Cheap DNA arrays–it's not all smoke and mirrors," Nature Biotech. 17(10):953.

Blanchard et al., 1996, "Sequence to array: probing the genome's secrets," Nat Biotechnol. 1996 Dec.;14(13):1649.

Blanchard, 1998, "Synthetic DNA arrays," Genet. Eng. (N. Y.) 20:111–23.

Bonaldo et al., 1996, "Normalization and subtraction: two approaches to facilitate gene discovery," Genome Res. 6(9):791–806.

Brett et al., 2000, "EST comparison indicated 38% of human mRNAs contain possible alternative splice forms," FEBS Lett. 474(1):83–6.

Bugawan et al., 1990, "Rapid HLA–DPB typing using enzymatically amplified DNA and nonradioactive sequence specific oligonucleotide probes", Immunogenetics 32: 231–241.

Bugawan et al., 1994, "A method for typing polymorphism at the HLA–A locus using PCR amplification and immobilized oligonucleotide probes," Tissue Antigens 44(3):137–47.

Burset M, 1996, "Evaluation of gene structure prediction programs," Genomics 34(3):353–67.

Caceres et al., 1994, "Regulation of alternative splicing in vivo by overexpression of antagonistic splicing factors," Science 265(5179):1706–9.

Caudevilla C, 1998, "Natural trans–splicing in carnitine octanoyltransferase pre–mRNAs in rat liver," Proc. Natl. Acad. Sci. U. S. A. 95(21):12185–90.

Chetverin and Kramer, 1994, "Oligonucleotide arrays: new concepts and possibilities," Biotech. (N Y) 12(11):1093–9.

Chirgwin et al., 1979, "Isolation of biologically active ribonucleic acid from sources enriched in ribonuclease," Biochem. 18(24):5294–9.

Choi et al., 2000, "The structure and expression of the murine wildtype p53–induced phosphatase 1 (Wip1) gene," Genomics 64(3):298–306.

Chutkow et al., 1999, "Alternative splicing of sur2 Exon 17 regulates nucleotide sensitivity of the ATP–sensitive potassium channel," J. Biol. Chem. 274(19):13656–65.

Claverie et al., 1999, "Computational methods for the identification of differential and coordinated gene expression," Hum. Mol. Genet. 8(10):1821–32.

Cronin et al., 1996, "Cystic fibrosis mutation detection by hybridization to light–generated DNA probe arrays," Hum. Mutat. 7(3):244–55.

DeRisi et al., 1996, "Use of a cDNA microarray to analyse gene expression patterns in human cancer," Nature Genet. 14(4):457–60.

Duggan et al., 1999, "Expression profiling using cDNA microarrays," Nat Genet. 1999 Jan.;21 (1 Suppl):10–4.

Dunham et al., 1999, "The DNA sequence of human chromosome 22," Nature 402(6761):489–95.

Egholm et al., 1993, "PNA hybridizes to complementary oligonucleotides obeying the Watson–Crick hydrogen–bonding rules," Nature 363:566–568.

Ewing et al., 2000, "Analysis of expressed sequence tags indicates 35,000 human genes," Nat Genet. 25(2):232–4.

Ferguson et al., 1996, "A fiber–optic DNA biosensor microarray for the analysis of gene expression," Nature Biotech. 14(13):1681–4.

Fisher et al., 1993, "Occurrence of a 2–bp (A1) deletion allete and a nonsense (G–to–T) mutant allele at the E2 (DBT) locus of six patients with maple syrup urine disease: multiple–exon skipping as a secondary effect of the mutations," Am. J. Hum. Genet. 52(2):414–24.

Fodor et al., 1991, "Light–directed, spatially addressable parallel chemical synthesis," Science 251(4995):767–73.

Friend and Bernards, 1986, "A human DNA segment with properties of the gene that predisposes to retinoblastoma and osteosarcoma," Nature 323(6089):643–6.

Froehler et al., 1986, "Synthesis of DNA via deoxynucleoside H–phosphonate intermediates," Nucleic Acids Res. 14(13): 5399–407.

Genbank Accesion No. L11910, Nov. 23, 1994.
Genbank Accession No. AF005058, Sep. 21, 2000.
Gracia et al., 1997, Isolation of chromosome–specific ESTs by microdissection–mediated cDNA capture. Genome Res. 7(2):100–7.
Guigo et al, 1992, "Prediction of gene structure," J. Mol. Biol. Jul. 5;226(1):141–57.
Gusella et al., 1983, "A polymorphic DNA marker genetically linked to Huntington's disease," Nature 306(5940):234–8.
Hacia et al., 1998, "Strategies for mutational analysis of the large multiexon ATM gene using high–density oligonucleotide arrays," Genome Res. 8(12):1245–58.
Hardison et al., 1997, "Long human–mouse sequence alignments reveal novel regulatory elements: a reason to sequence the mouse genome," Genome Res. 7(10):959–66.
Herbert et al., 1999, "RNA processing and the evolution of eukaryotes," Nature Genet. 21(3):265–9.
Hughes et al., 2000, "Functional discovery via a compendium of expression profiles," Cell 102(1):109–26.
Hutchinson et al., 1992, "The prediction of exons through an analysis of spliceable open reading frames," Nucleic Acids Res. 20(13):3453–62.
Jurka et al., 1998, "Repeats in genomic DNA: mining and meaning," Curr. Opin. Struct. Biol. 8(3):333–7.
Kamb et al., 1994, "Analysis of the p16 gene (CDKN2) as a candidate for the chromosome 9p melanoma susceptibility locus," Nature Genet. 8(1):23–6.
Khan et al., 1998, "Gene expression profiling of alveolar rhabdomyosarcoma with cDNA microarrays," Cancer Res. 58(22): 5099–13.
Koenigsberger et al., 2000, "Differential regulation by multiple promoters of the gene encoding the neuron–restrictive silencer factor," Proc. Natl. Acad. Sci. U. S. A. 97(5):2291–6.
Kruglyak et al., 1999, "Prospects for whole–genome linkage disequilibrium mapping of common disease genes," Nature Genet. 22(2):139–44.
Lehman et al., 2000, "Elevated frequency and functional activity of a specific germ–line p53 intron mutation in familial breast cancer," Cancer Res. 60(40):1062–9.
Lipshutz et al., 1999, "High density synthetic oligonucleotide arrays," Nature Genet. 21(1 Suppl):20–4.
Lockhart et al., 1996, "Expression monitoring by hybridization to high–density oligonucleotide arrays," Nature Biotech. 14(13):1675–80.
Maldonado–Rodriguez et al., 1999, "Hybridization of glass–tethered oligonucleotide probes to target strands pre-annealed with labeled auxiliary oligonucleotides," Mol. Biotechnol. 11(1):1–12.
Marton MJ, 1998; "Drug target validation and identification of secondary drug target effects using DNA microarrays," Nature Med. 4(11):1293–301.
Maskos and Southern, 1992, "Oligonucleotide hybridizations on glass supports: a novel linker for oligonucleotide synthesis and hybridization properties of oligonucleotides synthesized in situ," Nucleic Acids Res. 20(7):1679–84.
McBride et al., 1983, "An investigation of several deoxynucleoside phosphoramidites useful for synthesizing deoxyoligonucleotides," Tetrahedron Lett. 24:245–248.
Milner et al., 1997, "Selecting effective antisense reagents on combinatorial oligonucleotide arrays," Nature Biotech. 15(6): 537–41.

Nadal–Ginard et al., 1991, "Alternative Splicing is an Efficient Mechanism for the Generation of Protein Diversity: Contractile Protein Genes as a Model System," Adv. Enzyme Regul 261–285.
Nguyen et al., 1995, "Differential gene expression in the murine thymus assayed by quantitative hybridization of arrayed cDNA clones," Genomics 29(1):207–16.
Ohshima et al., 1987, "Signals for the selection of a splice site in pre–mRNA: Computer analysis of splice junction sequences and like sequences," J. Mol. Biol. 195(2):247–59.
Okamoto et al., 2000, "Microarray fabrication with covalent attachment of DNA using bubble jet technology," Nature Biotech. 18(4):438–41.
Pan and Heitman, 2000, "Sok2 regulates yeast pseudohyphal differentiation via a transcription factor cascade that regulates cell–cell adhesion," Mol. Cell. Biol. 22(11):8364–8372.
Parimoo et al., 1991, "cDNA selection: efficient PCR approach for the selection of cDNAs encoded in large chromosomal DNA fragments," Proc. Natl. Acad. Sci. U. S. A. 88(21):9623–7.
Pease et al., 1994, "Light–generated oligonucleotide arrays for rapid DNA sequence analysis," Proc. Natl. Acad. Sci. U. S. A. 91(11):5022–6.
Penn et al., 2000, "Mining the human genome using microarrays of open reading frames," Nature Genet. 26(3):315–8.
Pollack et al., 1999, "Genome–wide analysis of DNA copy–number changes using cDNA microarrays," Nature Genet. 23(1):41–6.
Potter and Dressler, 1986, "A 'Southern Cross' method for the analysis of genome organization and the localization of transcription units," Gene 48(2–3):229–39.
Reese et al., 2000, "Genome annotation assessment in *Drosophil melanogaster*," Genome Res. 10(4):483–501.
Reyes et a;/. 1991, "At least 27 alternatively spliced forms of the neural cell adhesion molecule mRNA are expressed during rat heart development," Mol. Cell. Biol. 11(3):1654–61.
Richmond et al., 1999, "Genome–wide expression profiling in *Escherichia coli* K–12," Nucleic Acids Res. 27(19):3821–35.
Roest et al., 2000, "Estimate of human gene number provided by genome–wide analysis using *Tetraodon nigroviridis* DNA sequence," Nature Genet. 25(2):235–8.
Rogozin et al., 1999, "Protein–coding regions prediction combining similarity searches and conservative evolutionary properties of protein–coding sequences," Gene 226(1):129–37.
Ross et al., 2000, "Systematic variation in gene expression patterns in human cancer cell lines," Nature Genet.24(3):227–35.
Schena et al., 1996, "Parallel human genome analysis: microarray–based expression monitoring of 1000 genes," Proc. Natl. Acad. Sci. U. S. A. 93(20):10614–9.
Schena et al., 1995, "Quantitative monitoring of gene expression patterns with a complementary DNA microarray," Science 270(5235):467–70.
Selinger et al., 2000, "RNA expression analysis using a 30 base pair resolution *Escherichia coli* genome array," Nature Biotech. 18(12):1262–8.
Shalon et al., 1996, "A DNA microarray system for analyzing complex DNA samples using two–color fluorescent probe hybridization," Genome Res. 6(7):639–45.

Snyder et al., 1993, "Identification of coding regions in genomic DNA sequences: an application of dynamic programming and neural networks," Nucleic Acids Res. 21(3):607–13.

Solovyev et al., 1994, "Predicting internal exons by oligonucleotide composition and discriminant analysis of spliceable open reading frames," Nucleic Acids Res. 22(24):5156–63.

Stark and Cooper, 1999, "The relative strengths of SR protein–mediated associations of alternative and constitutive exons can influence alternative splicing," J. Biol. Chem. 274(42):29838–42.

Stephan et al., 2000, "Positional cloning utilizing genomic DNA microarrays: the Niemann–Pick type C gene as a model system" Mol. Genet. Metab. 70(1):10–18.

Stickeler et al., 1999, "Stage–specific changes in SR splicing factors and alternitive splicing in mammary tumorigenesis," Oncogene 18(24):3574–82.

Strausberg et al., 1999, "The mammalian gene collection," Science 286(5439):455–7.

Takahashi et al., 2000, "Detection of aberrations of 17p and p53 gene in gastrointestinal cancers by dual (two–color) fluorescence in situ hybridization and GeneChip p53 assay," Cancer Genet. Cytogenet. 121(1):38–43.

Toguchida et al., 1993, "Complete genomic sequence of the human retinoblastoma susceptibility gene," Genomics 17(3):535–43.

Uberbacher and Mural RJ, 1991, "Locating protein–coding regions in human DNA sequences by a multiple sensor–neural network approach," Proc. Natl. Acad. Sci. U. S. A. 88(24):11261–5.

Usuka et al., 2000, "Gene structure prediction by spliced alignment of genomic DNA with protein sequences: increased accuracy by differential splice site scoring," J Mol Biol. 297(5):1075–85.

Velculescu et al., 1995, "Serial analysis of gene expression," Science 270(5235):484–7.

Viglianti et al., 1990, "Simian immunodeficiency virus displays complex patterns of RNA splicing," J. Virol. 64(9):4207–16.

Wang et al., 1998, "Large–scale identification, mapping, and genotyping of single–nucleotide polymorphisms in the human genome," Science 280(5366):1077–82.

Wegner et al., 1998, "Genomic organization and functional characterization of the chemokine receptor CXCR4, a major entry co–receptor for human immunodeficiency virus type 1," J. Biol. Chem. 273(8):4754–60.

Werner et al., 2001, "Target gene identification from expression array data by promoter analysis," Biomol. Eng. 17(3):87–94.

Winzler et al., 1998, "Direct allelic variation scanning of the yeast genome," Science. 281(5380):1194–7.

Yamanaka et al., 1997, "CCAAT/enhancer binding protein epsilon is preferentially up–regulated during granulocytic differentiation and its functional versatility is determined by alternative use of promoters and differential splicing," Proc. Natl. Acad. Sci. U. S. A. 94(12):6426–7.

Zhang MQ, 1998, "Statistical features of human exons and their flanking regions," Hum. Mol. Genet. 1998 7(5):919–32.

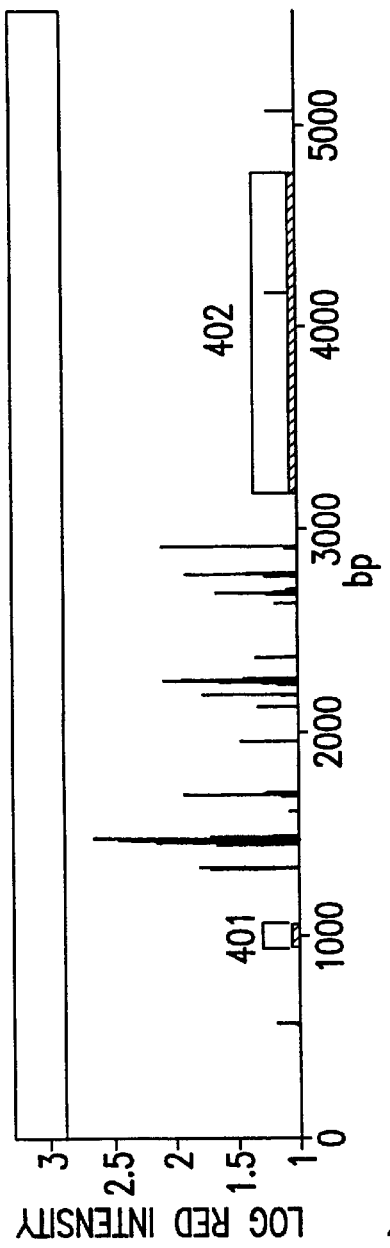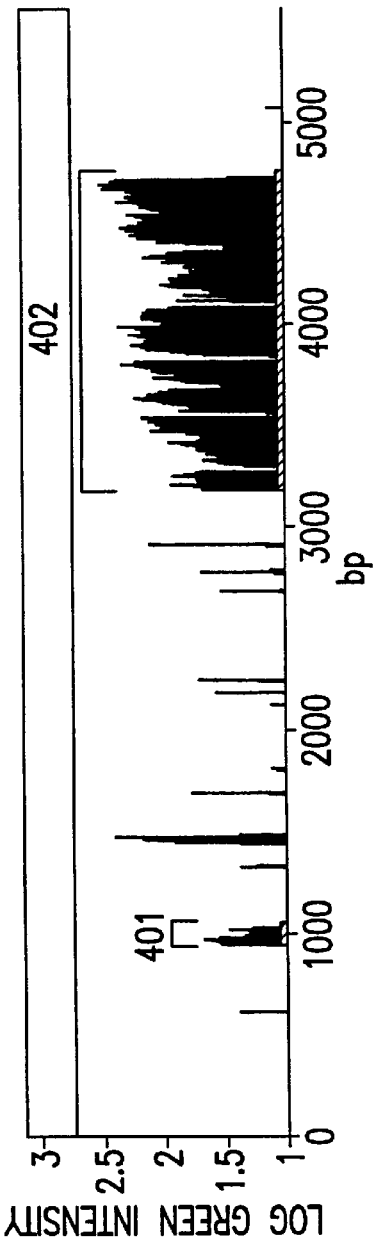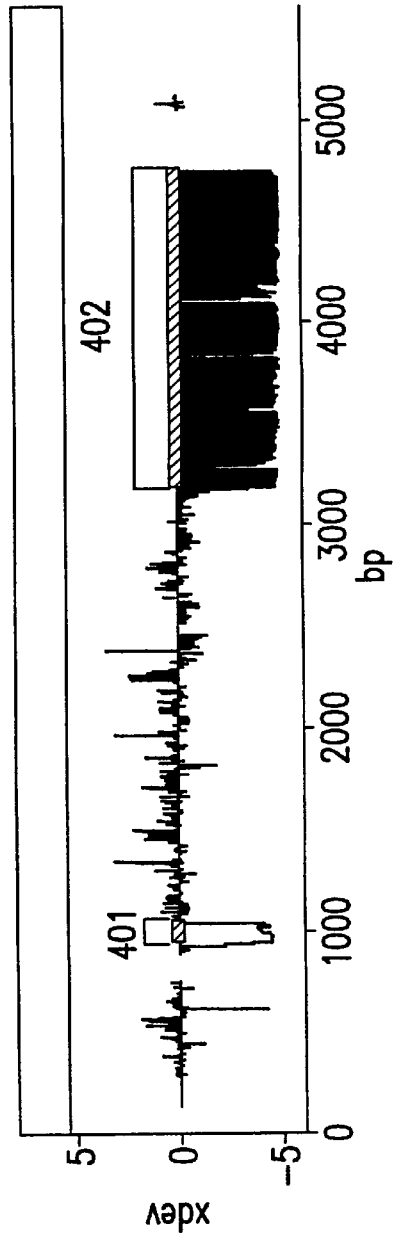

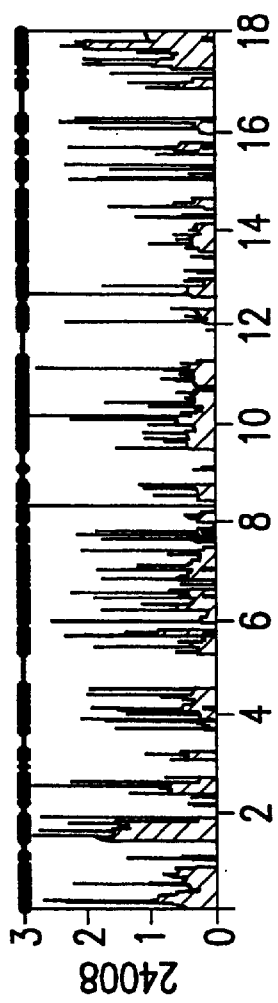
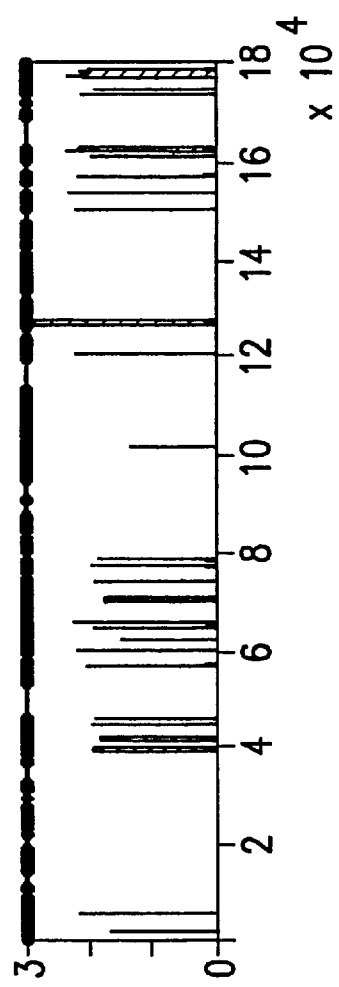
FIG. 10A
FIG. 10B

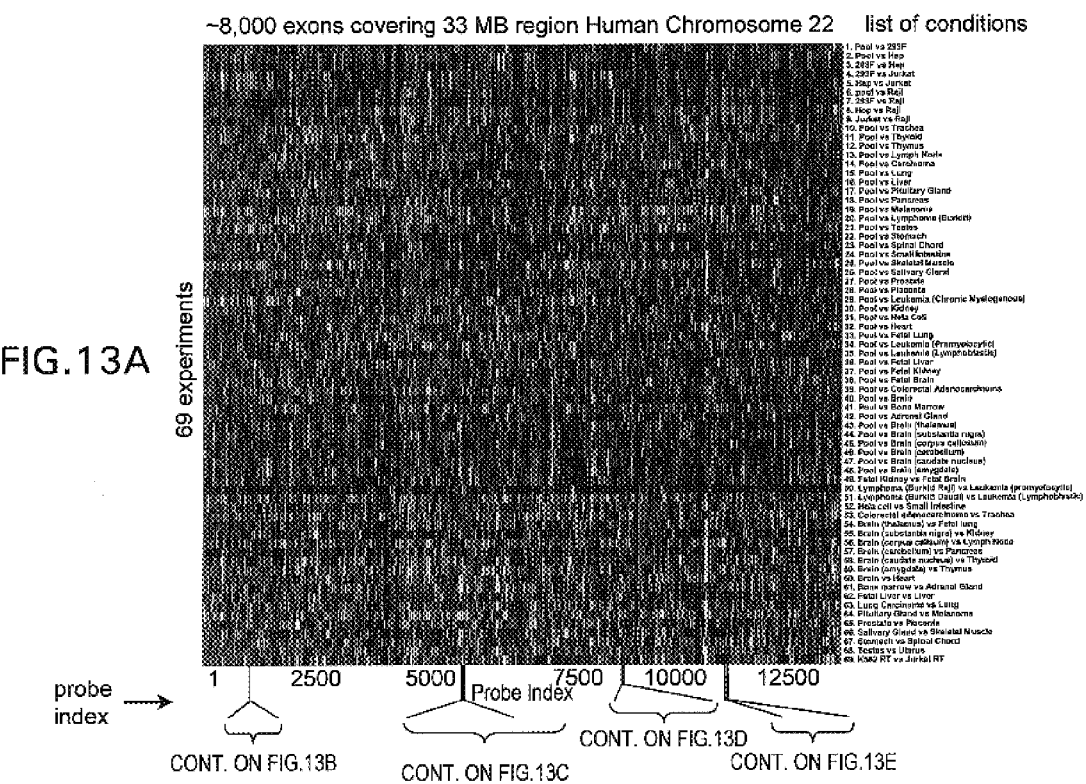

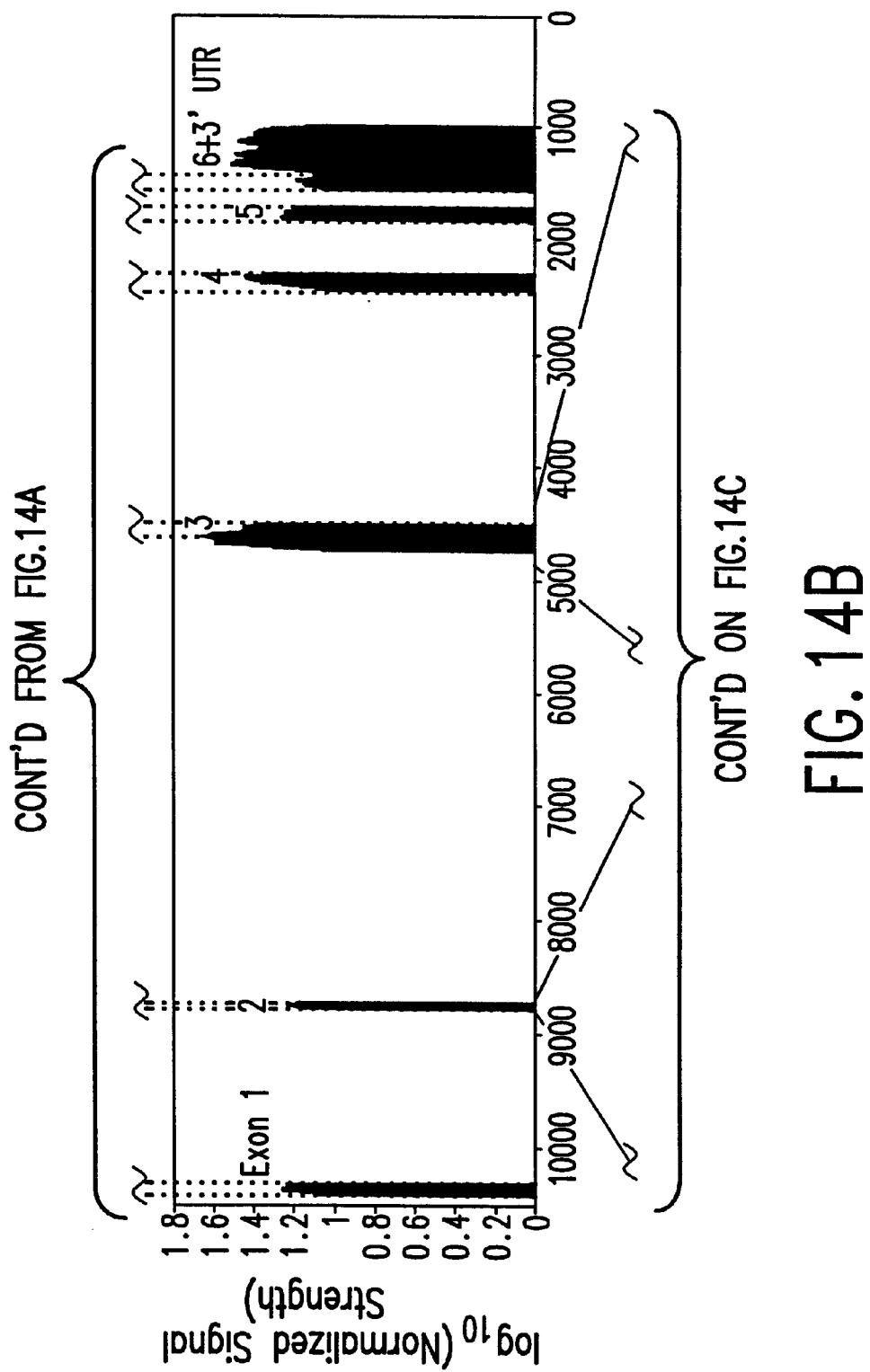

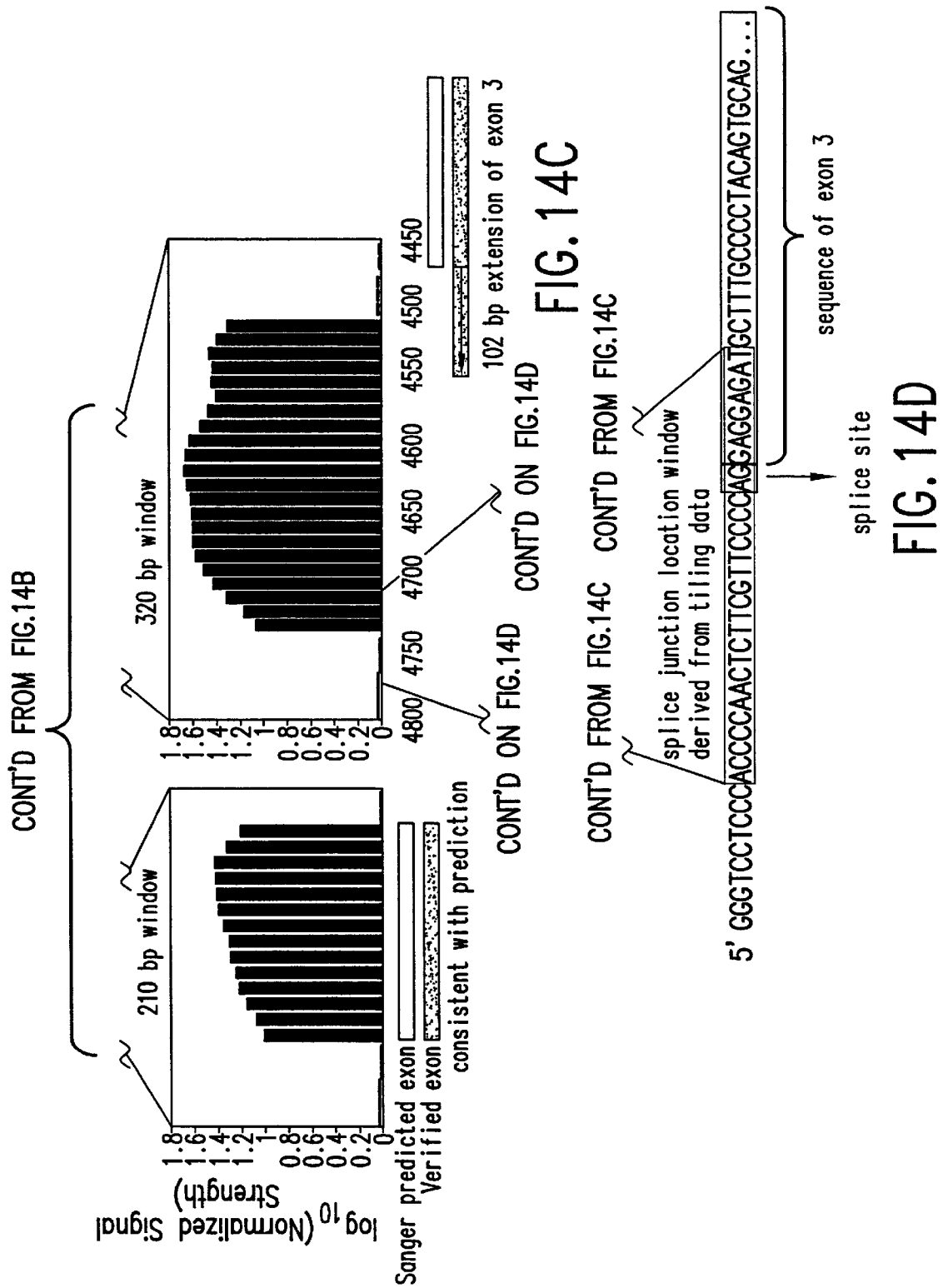

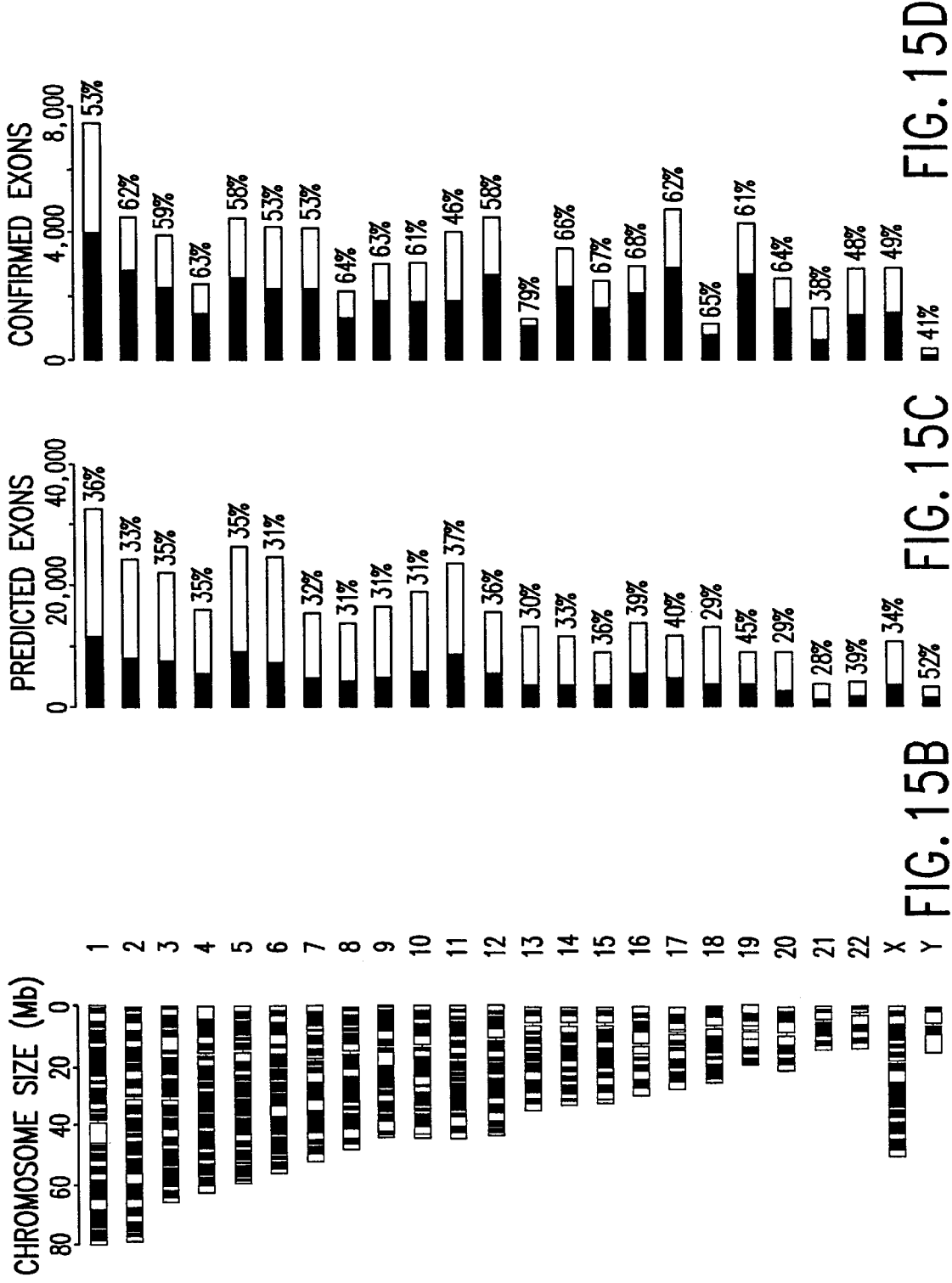

SEQUENCE LISTING

<160> NUMBER OF SEQ ID NOS: 1

<210> SEQ ID NO 1
<211> LENGTH: 60
<212> TYPE: DNA
<213> ORGANISM: Homo sapiens

<400> SEQUENCE: 1
gggtcctccc accccaactc ttcgttcccc aggaggagat gctttgcccc tacagtgcag      60

GENE DISCOVERY USING MICROARRAYS

This application claims benefit of U.S. Provisional Patent Application Ser. No. 60/227,966, filed on Aug. 25, 2000, and U.S. Provisional Patent Application Ser. No. 60/227,902, filed on Aug. 25, 2000, each of which is incorporated by reference herein in its entirety.

1. FIELD OF THE INVENTION

The present invention relates generally to the field of genomic analysis, and more particularly to methods for identifying and characterizing genes using microarrays.

2. BACKGROUND OF THE INVENTION

A fundamental goal of the human genome project is the identification and characterization of all genes in the genome. Knowledge of the location and structure of these genes has diverse applications, ranging from diagnostics and drug discovery through gene therapy. Genome projects for other species have similar goals and even more diverse applications, including increased food yields from plants and animals, production of industrially important proteins or metabolites, and development of new antimicrobial agents.

In bacterial and fungal genomes where only limited use of mRNA splicing is observed, most genes can be found simply by searching for open-reading-frames in the DNA sequence. Even in these simpler cases, problems are encountered in searching for small genes, reading frames that do not start the with the common AUG codon, and genes where translational frameshifting is used to control expression. In addition, finding genes via open-reading-frames is not effective when extensive splicing is seen and single genes can be spread across tens or even hundreds of kilobases of DNA. Moreover, regulatory sequences are often present in the untranslated regions at the ends of mRNAs, yet the reading-frame information is not helpful in locating such sequences.

Given a complex eukaryotic genome sequence, there are several known routes to gene discovery. Once the complete genome of an organism has been sequenced, the next step is to identify which regions of the genome are transcribed into mRNAs that code for proteins.

Until now, EST analysis has been the most powerful approach for identifying the transcribed regions of a sequenced genome. The process involves generating a large collection of cDNA clones from one or more tissues or growth conditions (see, e.g., Adams et al., 1991, Science 252:1651–6). The cloned sequences are tested with various sequence comparison algorithms to identify those that are parts of the same gene or represent different genes. Overlapping sequences representing a single gene are then merged to determine the sequence of the full length mRNA. The location of exons, or gene structure, can then be determined by simply mapping the mRNA sequence onto the genomic DNA. However, a major drawback of this approach is that some RNA species are produced at low levels or only in specific cells of an organism. Even with normalization methods to enrich for rarer RNAs, very large numbers of sequences from large numbers of tissues must be generated. Moreover, existing large collections of ESTs are often not uniformly distributed along the length of the gene because of the of the 3' bias caused by the oligo (dT)-primed reverse transcriptase (RT). For example, FIG. 2 shows a typical distribution of ESTs along a given human gene. Variants such as SAGE can yield much larger numbers of sequences, but this method only sequences a short region of each gene and relies on appropriately positioned restriction endonuclease cleavage sites (see, e.g., Velculescu et al., 1995, Science 270:484–7). Further, multiple RNA species can be derived from the same gene through differential splicing or other processing steps (see, e.g., Herbert and Rich, 1999, Nat. Genet. 21:265–9), making it difficult to obtain complete collections of mRNAs as full length cDNAs (see, e.g., Strausberg et al., 1999, Science 286:455–7).

Another experimental approach for identifying exons in genomic DNA involves hybridizing labeled mRNA to a microarray containing random genomic fragments. The genomic inserts that hybridize to the labeled mRNA are then sequenced and mapped back onto the chromosomal reference sequence (see, e.g., Stephan et al., 2000, Mol. Genet. Metab.70:10–18). While this approach has been successful in some cases, any clones will contain both introns and exons, making the procedure undesirable due to the very low resolution of the exon structure. Further, this method requires extensive DNA sequencing, and can only be used for relatively small genomic regions.

Hybrid selection is also another experimental method that can be used to identify transcribed regions of genomic DNA (see, e.g., Parimoo et al., 1991, Proc. Natl. Acad. Sci. 88:9623–7). Recent developments have expanded the number of genes that can be tested (see, e.g., Gracia et al., 1999, Genome Res. 7:100–7). However, the clones may only provide data on a small part of a gene.

Gene discovery can also be accomplished by comparing genomic sequences with known sequences from other species, making use of the evolutionary conservation of sequences with important functions (see, e.g., Rogozin et al., 1999, Gene 226:129–37; Hardison et al., 1997, Genome Res. 7:959–66; Nature Genetics Vol. 25 Num. 2, 235–8 (2000)). Such methods may prove successful for genes that are highly conserved, but will fail completely on the genes that are unique to a particular species.

In a similar manner, computer modeling may be used to develop models of gene structure and to scan new sequence data for suspected genes (see, e.g., Uberbacher and Mural, 1991, Proc. Natl. Acad. Sci. 88:11261–5; Snyder and Stormo, 1993, Nuc. Acids Res. 21:607–13). However, computer models will not succeed in identifying classes of genes that do not fit the assumptions of the models. Further, while such computer programs may frequently locate portions of genes, they cannot reliably or accurately predict the overall structure of a gene (see, e.g., Burset and Guigo, 1996, Genome Res. 15:353–67). Known errors include artifactually joining one gene with a neighboring gene of different function, failing to identify exons, predicting exons that do not exist, predicting the incorrect size of an exon, and splitting a single known gene into separate predicted genes (see, e.g., Reese et al., 2000, Genome Res. 10:483–501). Moreover, computer models are even more unreliable for genes that do not encode proteins, especially for long transcripts.

Thus, there exists a need for a high-throughput method for precisely identifying the location of genes in genomic sequences, especially genes that are transcribed at low levels. There also exists a need for a method of identifying and characterizing all of the elements of genes, especially genes that are spread over large regions of genomic DNA. Further, there exists a need for a method of characterizing the structure of genes without extensive DNA sequencing of ESTs. Even further, there exists a need for a method of correctly predicting the exact protein sequence based on the accurate structure of the gene. The methods and compositions of the present invention fulfill these needs and solve other problems in the prior art.

Discussion or citation of a reference herein shall not be construed as an admission that such reference is prior art to the present invention.

3. SUMMARY OF THE INVENTION

The present invention provides methods for identifying and characterizing the regions in genomic sequences that are transcribed into RNA. In particular, the invention provides improved, robust methods for detecting genes through the use of microarrays to analyze the expression state of the genome. Genes which are expressed can be mapped to their respective positions in the genome, and the structure of the gene determined.

The invention is premised, in part, upon the discovery that microarrays consisting of tiled genomic sequences can be employed to precisely identify the locations of expressed genes within the genome. In particular, an RNA or cDNA molecule will hybridize to probes on a microarray corresponding to the locations of the exons of the corresponding gene. Thus, the structure of the gene can be rapidly determined, even if the exons are widely separated in the genome or the gene is expressed at low levels. The invention is also partially premised upon the discovery that high resolution microarrays can be used to accurately determine intron-exon boundaries. Thus, by using the methods of the present invention, an accurate gene structure can be readily ascertained. Further, the methods of the present invention allow for the calculation of the probability that a particular nucleotide in a region of interest is expressed.

The present invention offers numerous advantages over the methods outlined above. First, the microarrays of the present invention enable an efficient and comprehensive genome scan that provides much more detailed data than prior art methods. Second, the methods of the present invention allow for the efficient identification of small genes, genes that do not encode proteins, genes that are transcribed at low levels, and untranslated regions of mRNAs encoding proteins. Third, the use of microarrays in the present invention allows the structure of the gene to be determined at the same time as the gene is detected, even if the gene is spread over large regions of the genome. Additional advantages and features of the invention will become apparent to one of skill in the art from the description and claims which follow.

4. BRIEF DESCRIPTION OF THE FIGURES

FIG. 1 illustrates a hypothetical strategy used to discover exons in a genomic sequence. 60-mer probes 104 are tiled in 15 bp steps 106 across a human genomic sequence for analysis of a hypothetical genomic region containing 2 exons, 101 and 102. After hybridizing labeled cDNA from a human cell line to an array 103, the positions of the exons 101 and 102 are determined by measuring the signal intensity at each of the probes 105.

FIG. 2 illustrates the genomic organization of the human CXCR-4 gene, which contains 2 exons 201 and 202 separated by an intron 203. Known EST sequences 204 are shown in relation to the genomic sequence.

FIG. 3 depicts a scanned image of a genomic scanning array according to the present invention. The 1×3 inch array 305 contains 25,000 different 60-mer probes. The region of the array showing the exact position of the two exons 301 and 302 of the CXCR-4 gene is shown in a enlargement 306. Control sequences 303 were synthesized along the perimeter of the array, and in diagonal stripes across the array. The first 60-mer from the region containing the CXCR-4 gene is located in the upper-left hand corner of the enlargement 306, and the chosen probe sequences are tiled in overlapping 5 bp steps across the array, ending at the bottom right hand corner of the enlargement 306. The reverse complement for each 60-mer was synthesized to the right of the position of each 60-mer. Cross-hybridization 304 can be seen at several points on the array.

FIG. 4 depicts the hybridization data from the genomic scanning array for the CXCR-4 gene. The x-axis shows the position for each of the different 60 mers and the y-axis shows the log intensity for each of the probes. Signal from the first exon is seen at 401, while signal from the second exon is seen at 402.

FIG. 4A depicts the log intensity of the Cy5 channel (K562) for each of the 910 60 mers tiled through the 5101 bp genomic region.

FIG. 4B depicts the log intensity of the Cy3 channel (Jurkat).

FIG. 4C depicts the error weighted ratio which filters out the cross-hybridization signals that were common to both channels and clearly shows the position of the two exons 401 and 402. The data from the reverse complement 60 mers is not shown.

Figure 5:
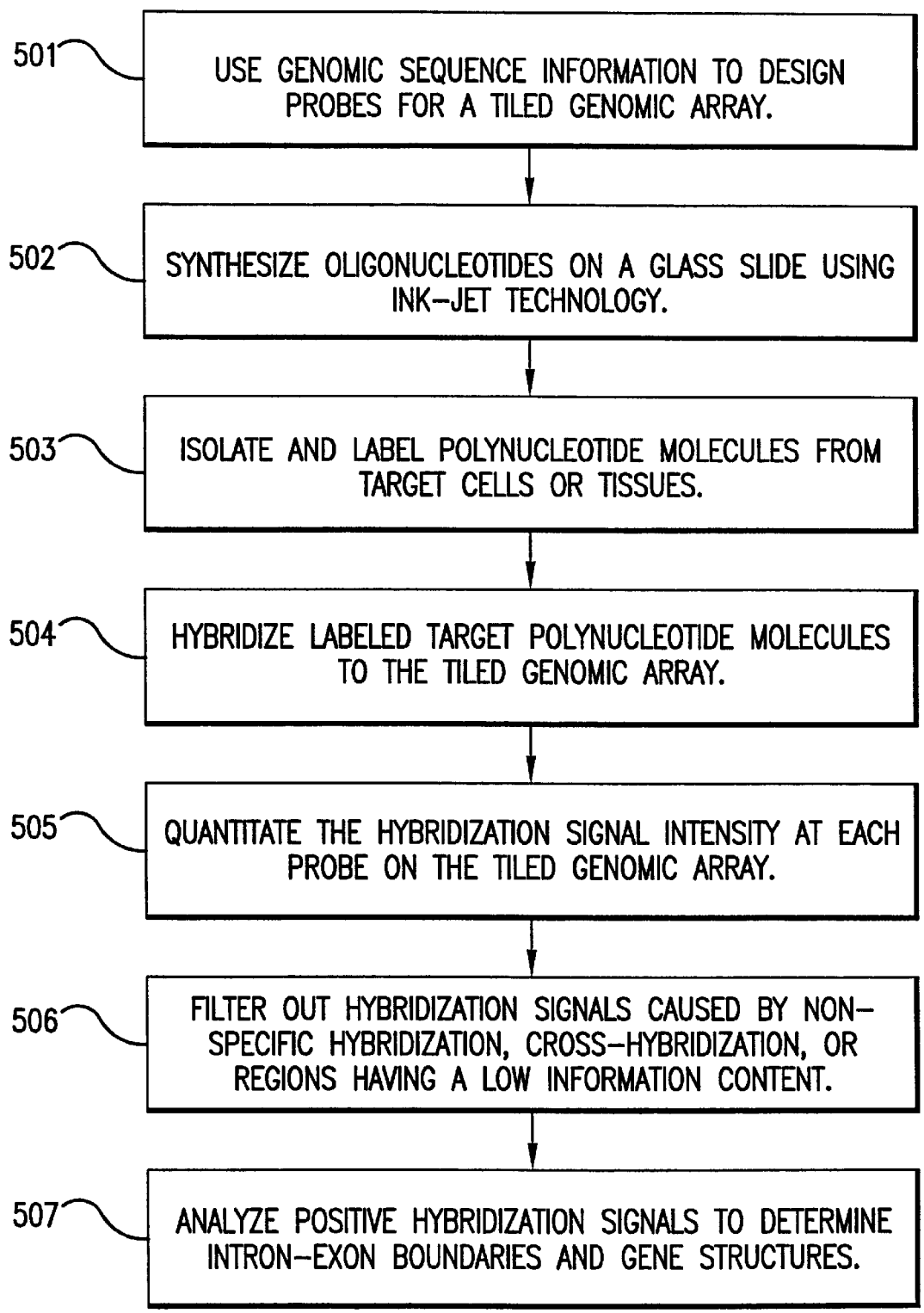

FIG. 5 is a flow chart diagram illustrating a detailed exemplary embodiment of the methods of the invention.

Figure 6:
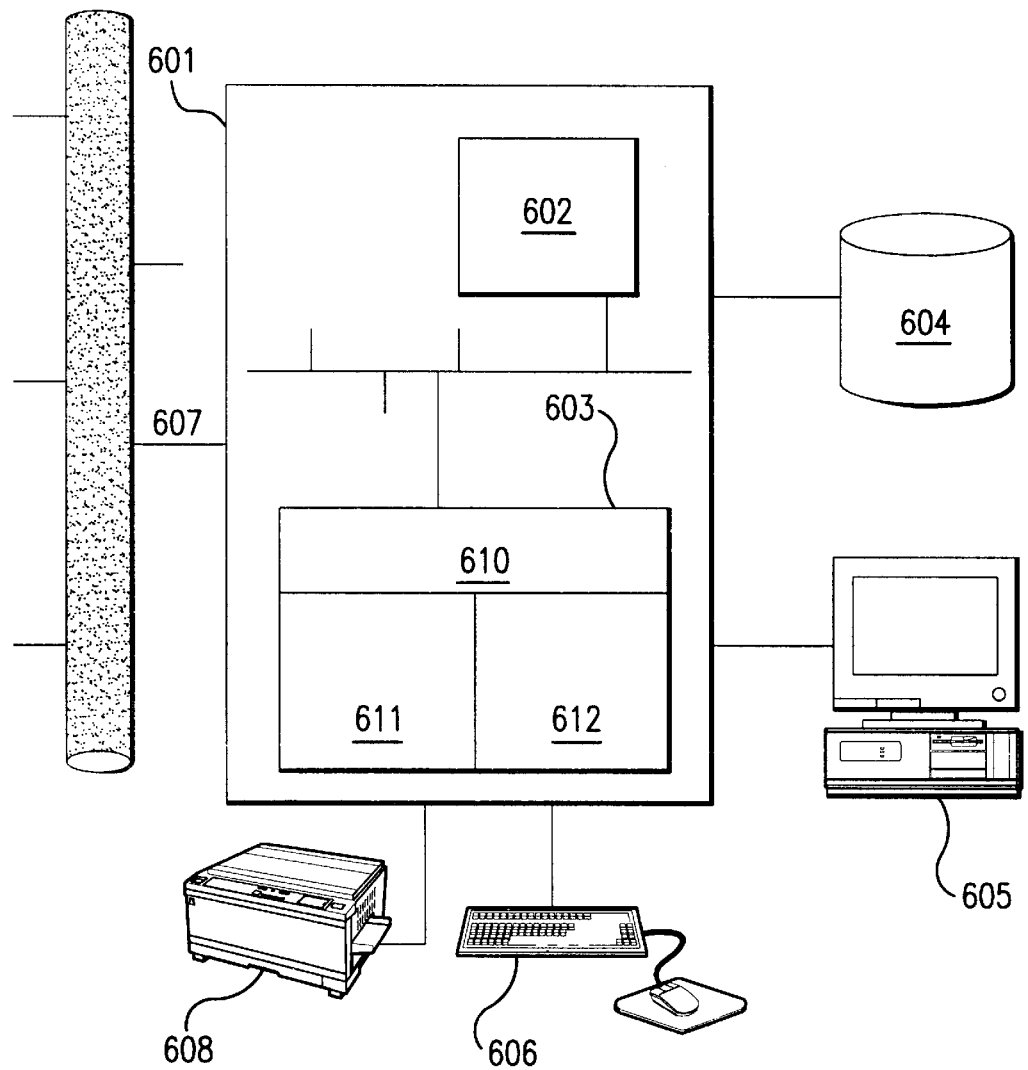

FIG. 6 illustrates an exemplary embodiment of a computer system useful for implementing the methods of the present invention. Illustrated is computer system 601 having the following components: processor unit 602; main memory 603; mass storage unit 604; user interface device 605; graphical input device 606; network link 607; printer 608; software component 610 (operating system); software component 611 (programming languages that can be used to program the analytic methods of the invention); and software component 612 (analytic methods of the present invention, preferably programmed in a procedural language or symbolic package).

FIG. 7 illustrates three exemplary embodiments of strategies used in the present invention.

Figure 7A:
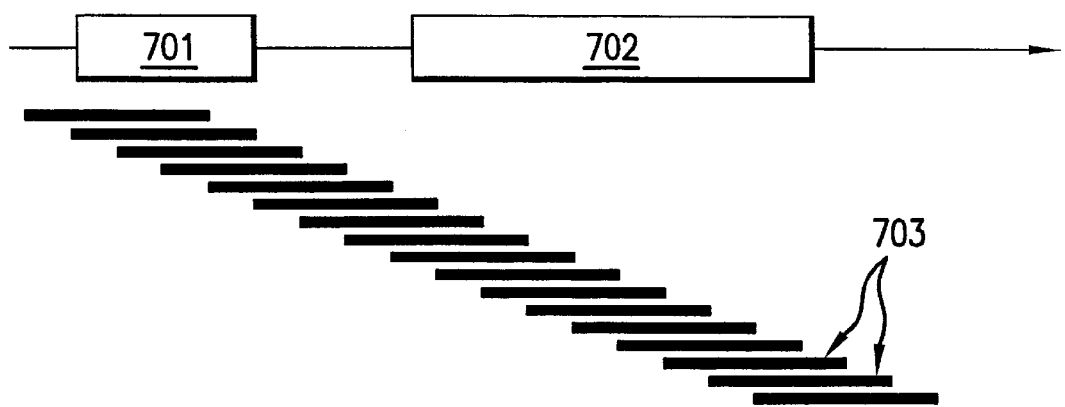

FIG. 7A provides an illustration of probes 703 tiled in an overlapping manner across a genome containing two exons 701 and 702.

Figure 7B:
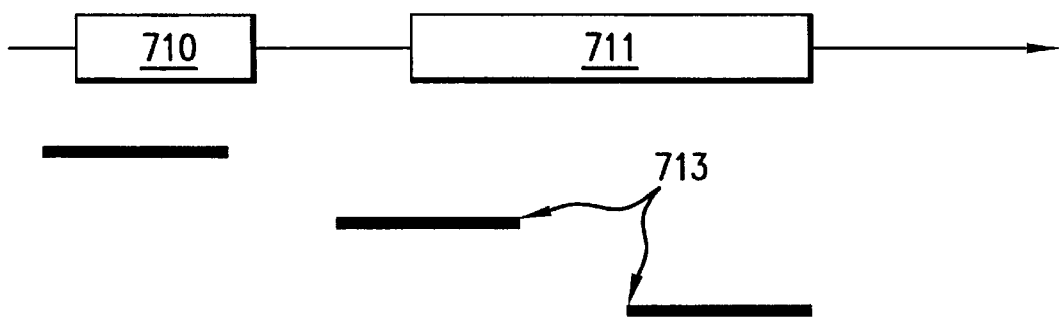

FIG. 7B provides an illustration of probes 713 tiled in an spaced manner across a genome containing two exons 711 and 712.

Figure 7C:
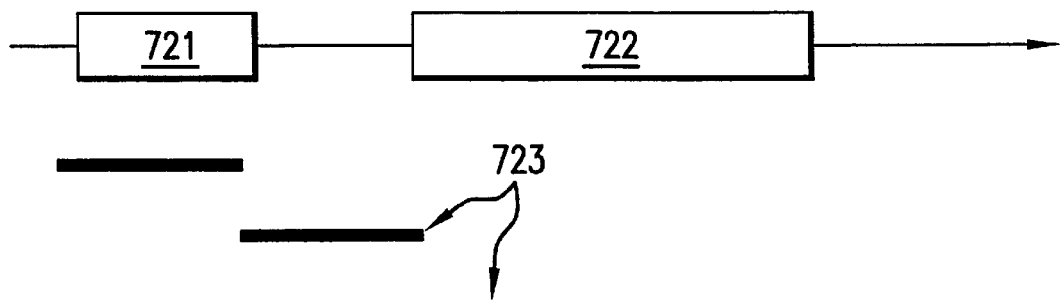

FIG. 7C provides an illustration of probes 723 tiled in an adjacent manner across a genome containing two exons 721 and 722.

Figure 8:
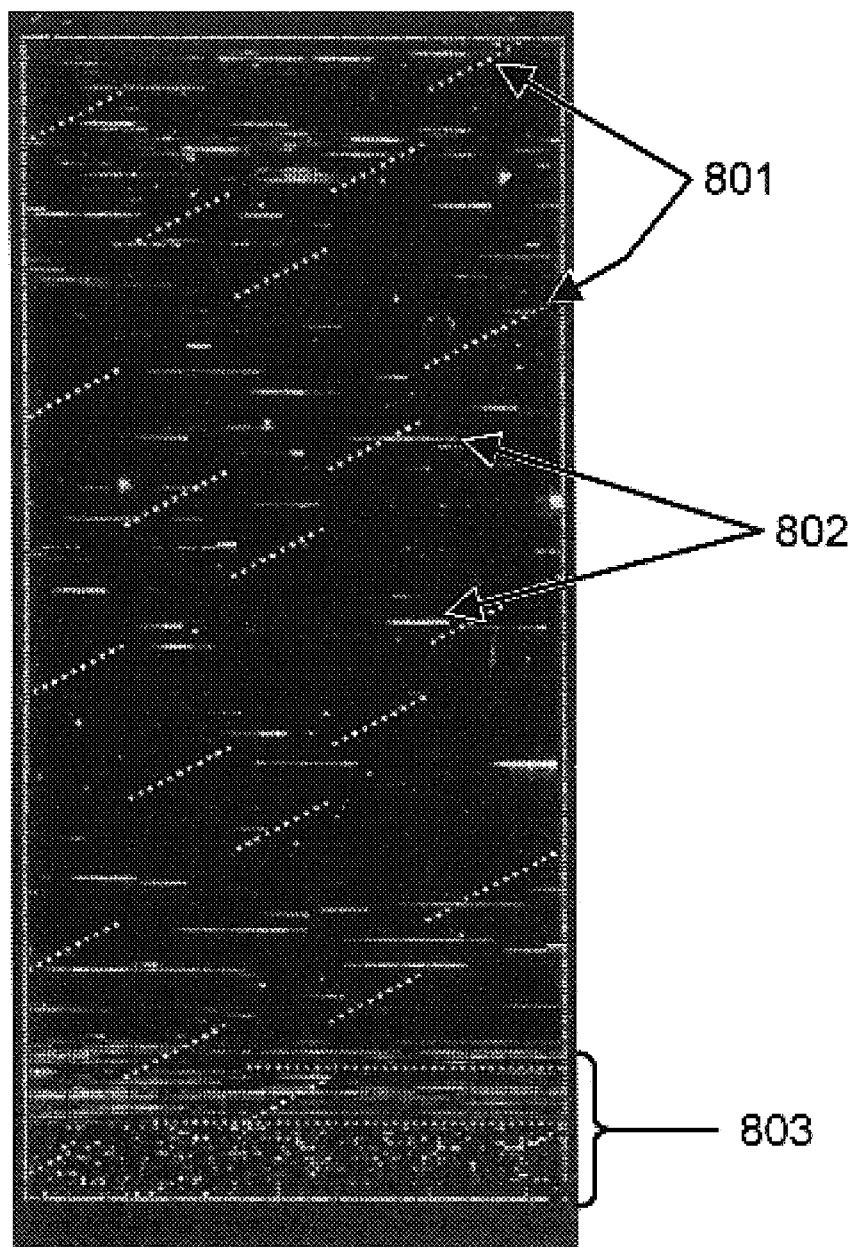

FIG. 8 depicts a scanned image of a genomic scanning array analysing the region containing the Rb1 gene according to the present invention. The 1×3 inch array contains about 25,000 different 60-mer probes. Control sequences 801 were synthesized along the perimeter of the array, and in diagonal stripes across the array. Probes 802 that show hybridization in a horizontal pattern represent exons. The dark areas between exons, showing no hybridization, represent introns. Control probes 803 were placed at the bottom of the array. The chosen probe sequences are tiled in overlapping 8 bp steps across the array. The reverse complement for each 60-mer was synthesized to the right of the position of each 60-mer. Cross-hybridization can be seen at several points on the array.

FIG. 9 depicts the degree of detected hybridization (in log intensities) of cDNA from Jurkat cells (known to express the Rb gene) to each of the probes on the genomic scanning array described for FIG. 8, plotted relative to the base pair location of this region of human chromosome 13. Sets of 60 mer probes complementary to the expressed mRNA sequence and to the reverse complement DNA strand were tiled in overlapping 8 bp steps and printed on the same array, with some probes omitted due to regions of repetitive sequence. Dots 901 along the top of each graph indicate the position along the 180 kb region of genomic DNA where probes were printed (as noted, probes containing regions of low information content were not printed). Small vertical bars 902 along the bottom of each graph indicate the location of the 28 known exons for the Rb gene.

Figure 9A:
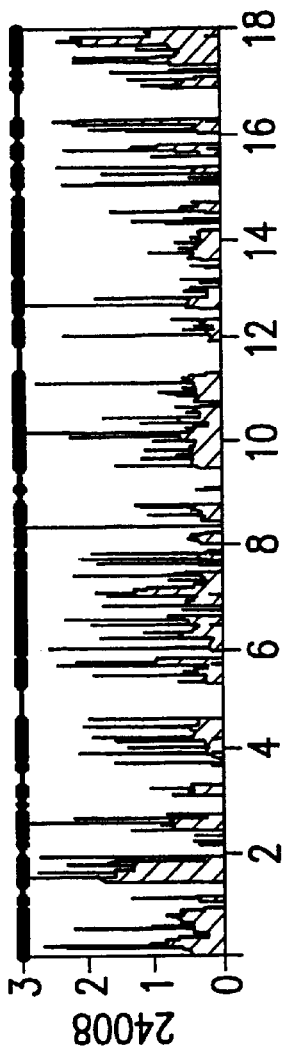

FIG. 9A depicts the log intensity for each of the 60 mer probes complementary to the coding strand in genomic sequence.

Figure 9B:
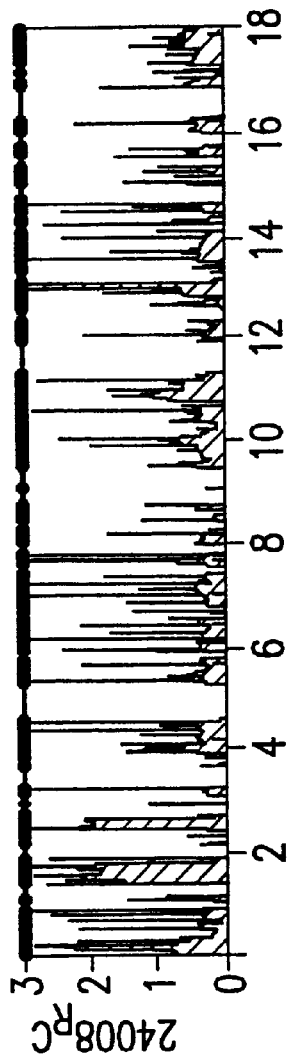

FIG. 9B depicts the log intensity for each of the reverse complements for each of the different 60 mer probes.

FIG. 10 depicts the degree of detected hybridization (in log intensities) of cDNA from Jurkat cells (known to express the Rb gene) to each of the probes on the genomic scanning array described for FIG. 8, plotted relative to the base pair location of this region of human chromosome 13, both before and after processing using the Complementary Strand Filtering Method of the invention. The filtering algorithm parameters chosen were a rectangular window of total width 9 for each strand, and a difference threshold algorithm with d=1. The results were post-processed with a median filter of total width 3. Dots 1001 along the top of each graph indicate the position along the 180 kb region of genomic DNA where probes were printed. Small vertical bars 1002 along the bottom of each graph indicate the location of the 28 known exons for the Rb gene.

FIG. 10A depicts the log intensity for each of the 60 mer probes complementary to the coding strand of the genomic region encoding the Rb1 gene prior to application of the Complementary Strand Filtering Method.

FIG. 10B depicts the same hybridization data after processing the data using the above-described algorithm in the Complementary Strand Filtering Method.

FIG. 11 depicts hybridization data obtained from three different samples of RNA from Jurkat cells known to express the Rb gene (FIGS. 11A–C) and one sample of RNA from K562 cells in which the Rb gene is not expressed at significant levels (FIG. 11D) that were analyzed using the scanning array and methods as described for FIG. 8 after processing using the Complementary Strand Filtering Method as described for FIG. 10. The filtering algorithm parameters chosen were a rectangular window of total width 9 for each strand, and a difference threshold algorithm with d=1. The results were post-processed with a median filter of total width 3. Dots 1101 along the top of each graph indicate the position along the 180 kb region of genomic DNA where probes were printed. Small vertical bars 1102 along the bottom of each graph indicate the location of the 28 known exons for the Rb gene.

Figure 11A:
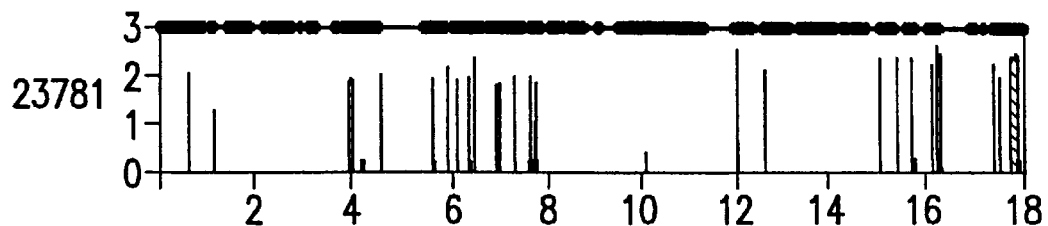
Figure 11B:
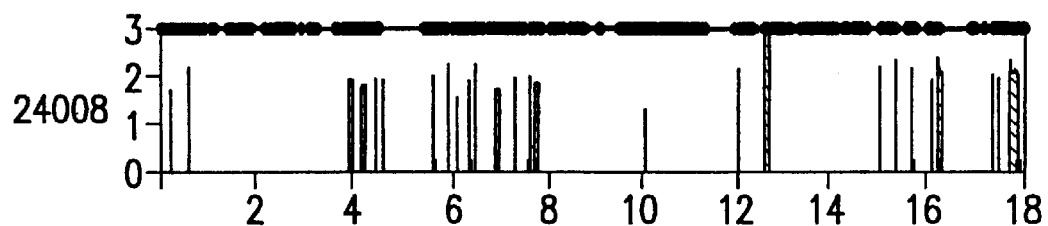
Figure 11C:
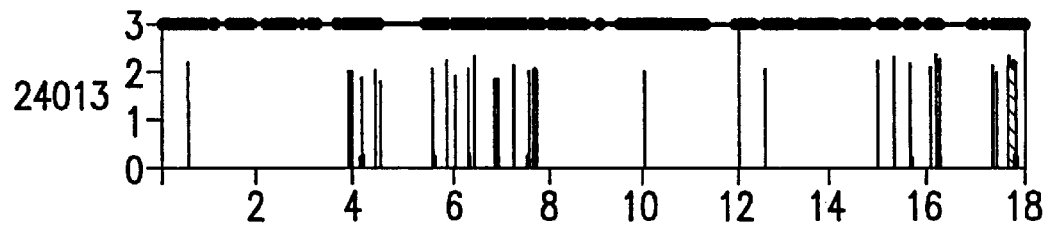

FIGS. 11A–C depict the log intensity of the hybridization signal for three samples of cDNA derived from RNA from Jurkat cells to each of the 60 mer probes complementary to the coding strand of the genomic region encoding the Rb1 gene after application of the Complementary Strand Filtering Method; FIG. 11B depicts the same data as in FIG. 10B.

Figure 11D:
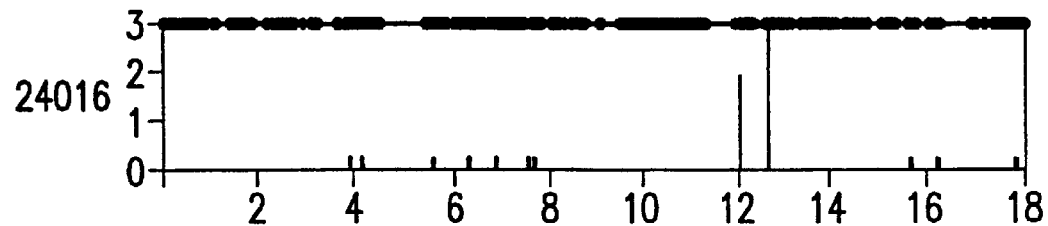

FIG. 11D depicts the log intensity of the hybridization signal for a sample of cDNA derived from RNA from K562 cells to each of the 60 mer probes complementary to the coding strand of the genomic region encoding the Rb1 gene after application of the Complementary Strand Filtering Method.

Figure 12:
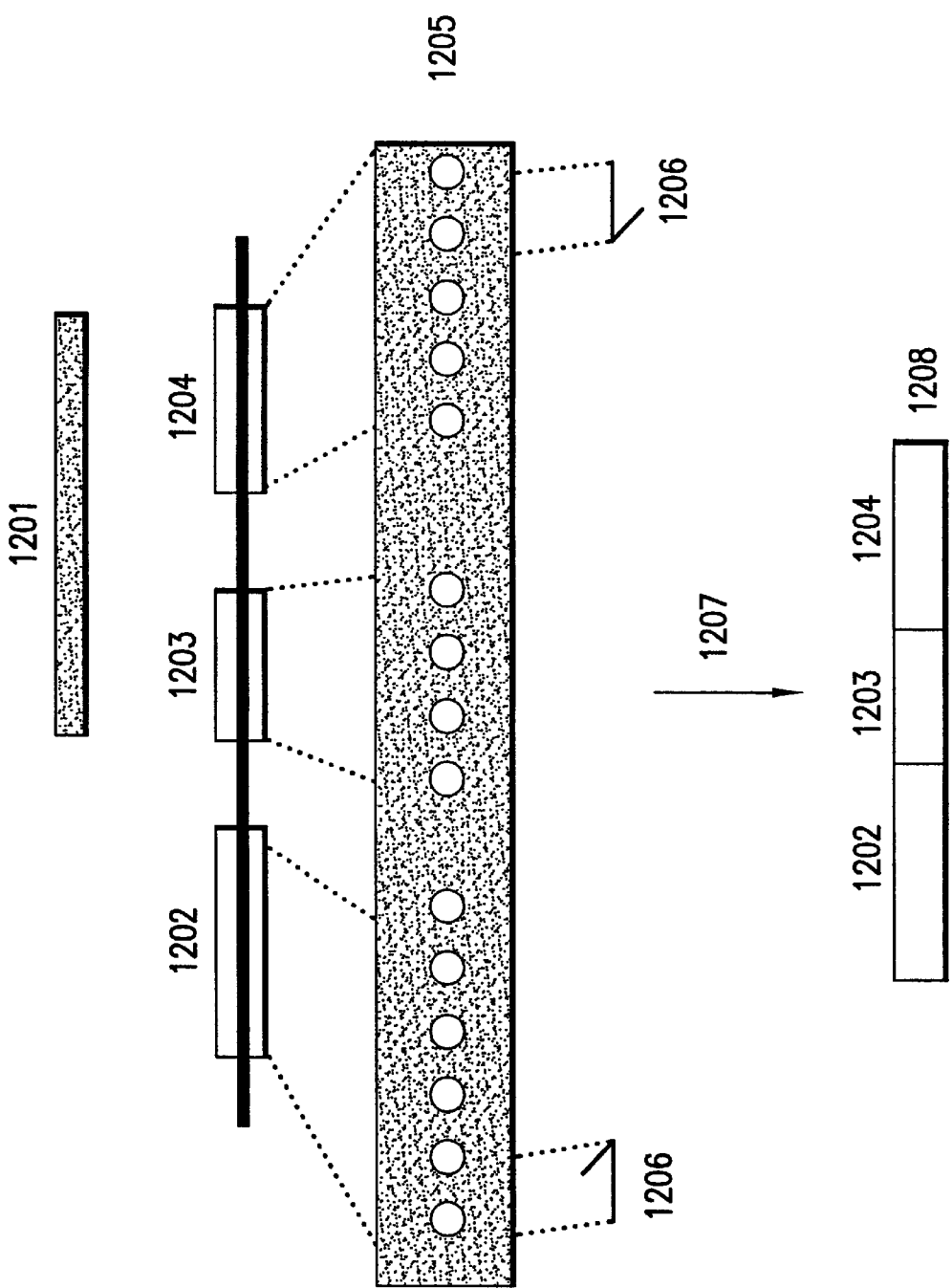

FIG. 12 illustrates the use of an exemplary embodiment of the scanning strategies of the present invention to identify an unknown exon by extension of a known EST sequence. A hypothetical gene comprises three exons 1202–1204. Exons 1203 and 1204 are contained in a known EST 1201, but exon 1202 is unknown. When the region of the genome containing exons 1202–1204 is tiled on a genomic scanning array 1205 according to the methods of the present invention, hybridization is detected for exons 1202–1204. To confirm that the signal detected for exon 1202 indicates a novel exon, a pair of PCR primers 1206 is designed to amplify the predicted full-length product. After RT-PCR 1207 with the primers 1206 and cDNA template from a tissue source expressing the known EST 1201, the full-length product 1208 is obtained, confirming that exon 1202 is part of the gene encoding known EST 1201.

Figures 13B, 13C, 13D, 13E:
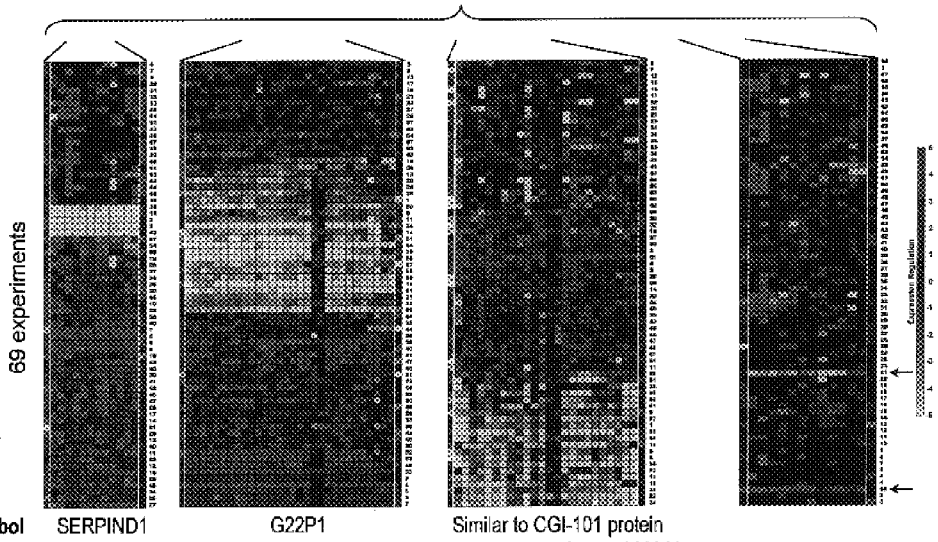

FIGS. 13A–E depict an exemplary use of screening arrays using expression data from multiple conditions to validate exons and define gene boundaries on chromosome 22. FIG. 13A depicts an array image showing $\log_{10}$ expression ratios for each of the ~8,000 exons (x-axis) across the 69 fluor reversed experiments (y-axis). In this Figure, downregulation of the Cy3 channel relative to the Cy5 channel is represented generally as lighter shades of gray; upregulation of the Cy3 channel relative to the Cy5 channel is represented generally as darker shades of gray. A brief description of sixty-nine two-condition experiments is listed on the right side of the image along with numbers that serve as reference points for FIGS. 13B–E. FIG. 13B depicts an expanded region that includes a known gene, SERPIND1 (Accession No. NM_000185). The experiments on the y-axis are clustered to emphasize how co-regulation across diverse experiments can be used to group exons into genes. The vertical white lines show the boundaries predicted by the gene finding algorithm using scanning data. FIG. 13C shows an expanded region containing a set of co-regulated exons from another known gene, G22P1 (Accession No. NM_001469). A potential false exon prediction made by the Genscan prediction program is indicated by the arrow. FIG. 13D shows an expanded region verified gene that collapses two Unigene EST clusters, HS.269963 and HS.14587, into a single transcript. FIG. 13E shows an expanded region containing a verified gene possessing six exons that are part of a novel transcript that is expressed in the testis. Arrows indicate the position of the two experiments involving testis RNA samples.

Figure 14A:
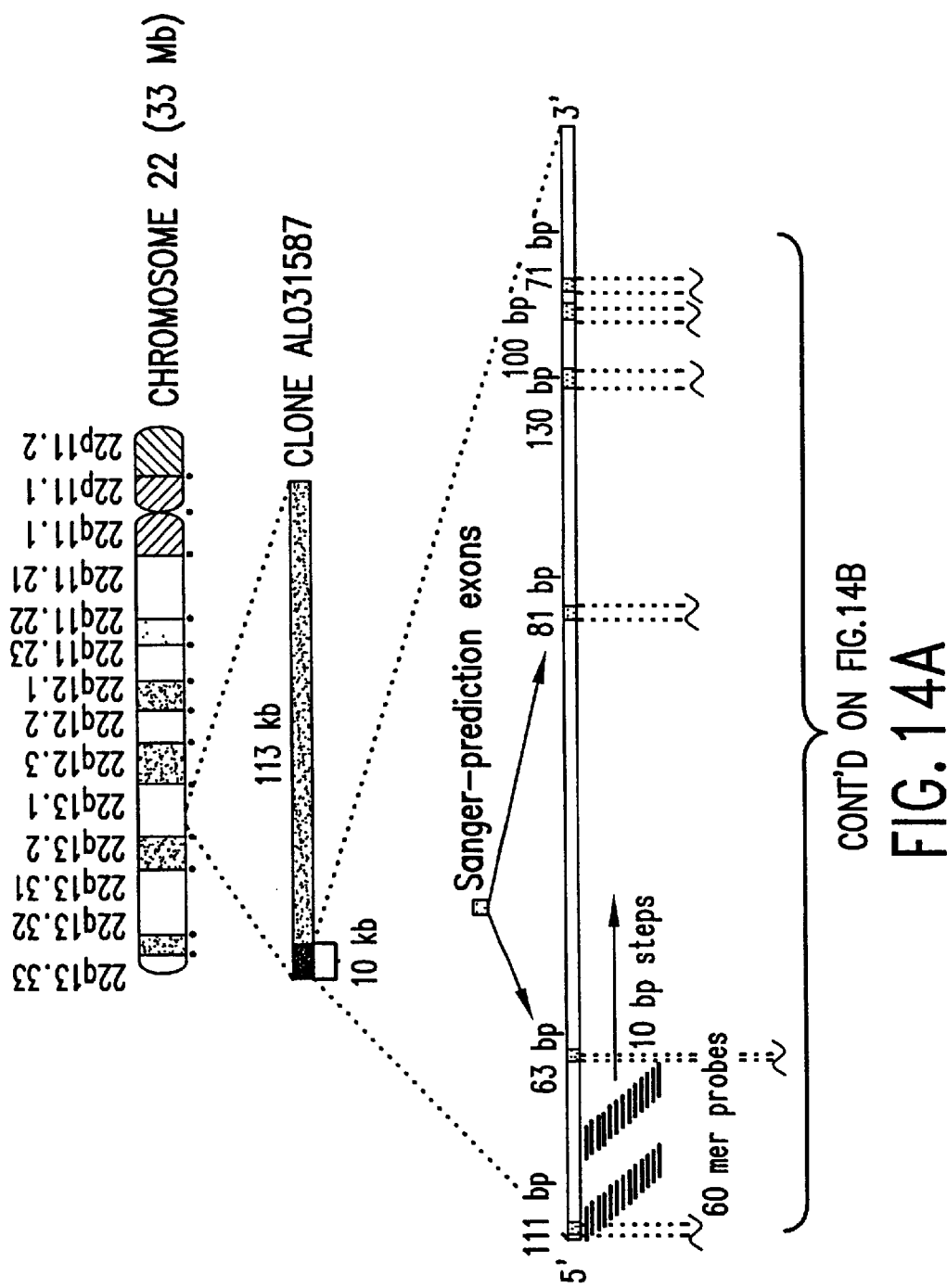

FIGS. 14A–D depict the characterization of a novel testis transcript using scanning arrays. An Expression Verified Gene (EVG; see Example 5) discovered in the analysis of chromosome 22 was localized to a 10 kb region at one end of the insert of BAC clone AL031587 (FIG. 14A). Following the described method, both strands of this 113 kb genomic interval were tiled with 60 mer probes placed in 10 bp intervals. The scanning array was hybridized with RNA isolated from human testis. Hybridization signals corresponding to scanning probes from this region were filtered and plotted as $\log_{10}$ values of the normalized signal strengths (FIG. 14B). Detailed views of scanning data showing one correctly predicted exon and one incorrectly predicted exon are shown in FIG. 14C. After narrowing the search window for a given intron/exon boundary down to a 20–30 bp region using scanning data, the exact splice junction was then identified using a combination of consensus sequences (GT-AG rule) and ORF information. FIG. 14D presents the sequence of a segment of chromosome 22 DNA (SEQ ID NO: 1) containing the 3' end of an intron (left), the "AG" splice site signal, and the 5' end of the sequence of exon 3.

Figure 15A:
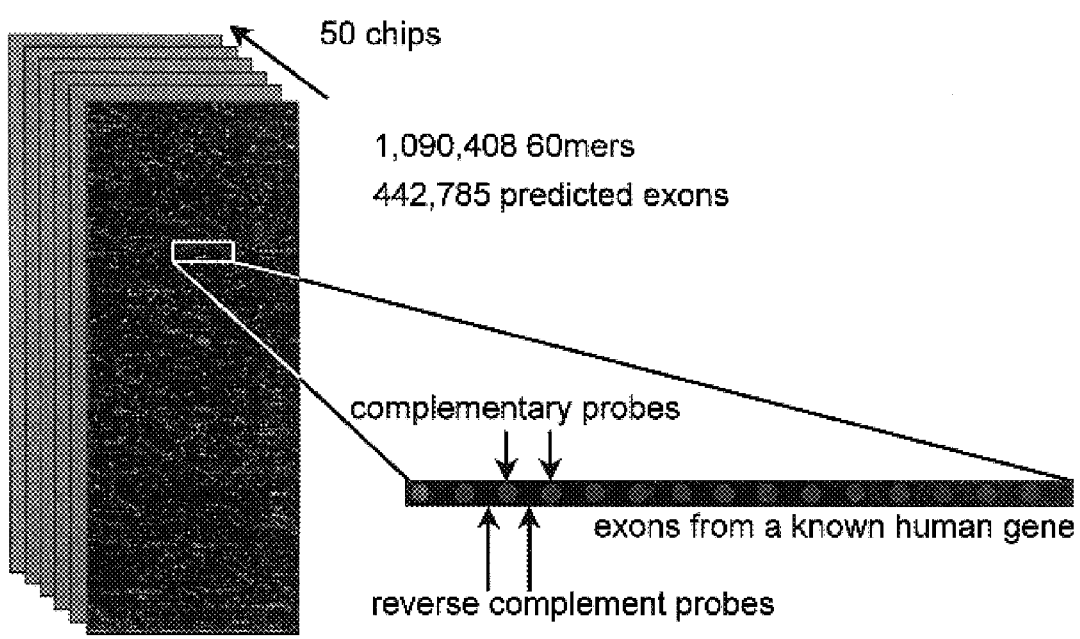

FIGS. 15A–D depict a whole-genome screen for validating predicted exons. In FIG. 15A, a set of 50 1×3 inch ink-jet printing-produced arrays were used to experimentally test 442,785 exons predicted by the Genscan program under two conditions. For each predicted exon, the best one or two 60 mer probes were selected resulting in the set of 1,090,408 probes which were distributed over 50 different arrays (~25,000 60 mers per array). The arrays also included 110,000 reverse complement probes and 48,500 control probes. The arrays were hybridized with Cy-3 or Cy-5 labeled mRNA from human B lymphocyte and colorectal adenocarcinoma cell lines. The enlarged image to the right shows probes representing exons from a known gene with alternating perfect match and reverse complement probes. All experiments were performed in duplicate with a fluor reversal (100 arrays total). FIG. 15B depicts the sizes of the different human chromosomes. FIG. 15C shows the number of predicted exons that were experimentally verified (dark gray bars) for each of the chromosomes. The light gray bars indicate the total number of predicted exons on each chromosome. FIG. 15D shows a the number of confirmed exons across the human genome. Dark gray bars indicate exons verified, and light gray bars indicate the total number of confirmed exons.

5. DETAILED DESCRIPTION OF THE INVENTION

This section presents a detailed description of the invention and its applications. The description is by way of several exemplary illustrations, in increasing detail and specificity, of the general methods of this invention. These examples are non-limiting, and related variants will be apparent to one of skill in the art.

Although, for simplicity, this disclosure make references to the genomes of particular organisms, it will be understood by those skilled in the art that the methods of the present invention are useful for the identification and characterization of genes from the genome of any organism, and particularly useful with eukaryotic organisms.

5.1. Introduction

The inventors have discovered that microarrays consisting of tiled genomic sequences can be employed to precisely identify the locations of expressed genes within the genome, and also to verify predicted or known locations within the genome for expressed genes. In particular, the RNA from a given biological sample (or corresponding cDNA) will hybridize to the probes on such a microarray corresponding to the locations of the exons of all genes expressed in that biological sample. Thus, by analyzing RNA samples from diverse tissues and growth conditions, all of the expressed genes within a genome can be rapidly identified and localized. The invention is also based in part on the inventors' discovery that the structure of a given gene can be rapidly determined by analysis of the locations of expressed exons in the genomic DNA. In particular, once the locations of the exons of a gene have been determined or verified, high-resolution microarrays can be used to accurately determine intron-exon boundaries. Thus, by using the methods of the present invention, an accurate gene structure can be readily ascertained.

This section first presents general concepts related to the invention, as well as definitions of specific terms used herein. The following sections present specific non-limiting embodiments of this invention in greater detail.

5.1.1 Definitions

As used in herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms.

A "gene" is identified as the portion of DNA that is transcribed by RNA polymerase. Thus, a gene may include a 5' untranslated region ("UTR"), introns, exons and a 3' UTR.

5.2 Methods for Identifying Genes in a Genomic Sequence

The present invention provides methods for identifying and characterizing genes in genomic sequences. In particular, the invention provides improved, robust methods for detecting genes through the use of microarrays to analyze the transcriptional state of the genome. Expressed genes can be mapped to their respective positions in the genome, and the structure of the gene determined.

The inventors have discovered that microarrays consisting of tiled genomic sequences can be employed to precisely identify the locations of expressed genes within the genome, and also to verify predicted or known locations within the genome for expressed genes. In particular, the RNA from a given biological sample (or corresponding cDNA or RNA derived therefrom) will hybridize to the probes on such a microarray corresponding to the locations of the sequences expressed in that biological sample. Thus, by analyzing RNA samples from diverse tissues and growth conditions, all of the expressed genes within a genome can be rapidly identified and localized. The inventors have also discovered that the structure of a given gene can be rapidly determined by analysis of the locations of expressed exons. In particular, once the locations of the exons of a gene have been determined or verified, high-resolution microarrays or other analytical methods can be used to accurately determine intron-exon boundaries. Thus, by using the methods of the present invention, an accurate gene structure can be readily ascertained, even if the gene has multiple RNA species or is extensively processed.

5.2.1 Construction of Microarrays

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support which may be either porous or non-porous. For example, the probes of the invention may be polynucleotide sequences which are attached to a nitrocellulose or nylon membrane or filter covalently at either the 3' or the 5' end of the polynucleotide. Such hybridization probes are well known in the art (see, e.g., Sambrook et al., Eds., 1989, *Molecular Cloning: A Laboratory Manual*, 2nd ed., Vol. 1–3, Cold Spring Harbor Laboratory, Cold Spring Harbor, N.Y.). Alternatively, the solid support or surface may be a glass or plastic surface. In a particularly preferred embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In preferred embodiments, a microarray comprises a support or surface with an ordered array of binding (e.g., hybridization) sites or "probes" that tile across the genomic DNA of an organism. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). In preferred embodiments, each probe is covalently attached to the solid support at a single site.

Microarrays can be made in a number of ways, of which several are described below. However produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 1 $cm^2$ and 25 $cm^2$, between 12 $cm^2$ and 13 $cm^2$, or 3 $cm^2$. However, larger arrays are also contemplated and may be preferable, e.g., for use in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

The microarrays of the present invention include one or more test probes, each of which has a polynucleotide sequence that is complementary to a subsequence of RNA or DNA to be detected. Preferably, the position of each probe on the solid surface is known. Indeed, the microarrays are preferably positionally addressable arrays. Specifically, each probe of the array is preferably located at a known, predetermined position on the solid support such that the identity (i.e., the sequence) of each probe can be determined from its position on the array (i.e., on the support or surface).

Preferably, the density of probes on a microarray is about 150 different (i.e., non-identical) probes per 1 $cm^2$ or higher. More preferably, a microarray of the invention will have at least 550 different probes per 1 $cm^2$, at least 1,000 different probes per 1 $cm^2$, at least 1,500 different probes per 1 $cm^2$ or at least 2,000 different probes per 1 $cm^2$. In a particularly preferred embodiment, the microarray is a high density array, preferably having a density of at least about 2,500 different probes per 1 $cm^2$. The microarrays of the invention therefore preferably contain at least 2,500, at least 5,000, at least 10,000, at least 15,000, at least 20,000, at least 25,000, at least 50,000, at least 55,000, at least 100,000 or at least 150,000 different probes.

In specific embodiments, the density of probes on a microarray is between about 150 and 1,000 different (i.e., non-identical) probes per 1 $cm^2$, between 1,000 and 5,000 different probes per 1 $cm^2$, between 5,000 and 10,000 different probes per 1 $cm^2$, between 10,000 and 15,000 different probes per 1 $cm^2$, between 15,000 and 20,000 different probes per 1 $cm^2$, between 20,000 and 50,000 different probes per 1 $cm^2$, between 50,000 and 100,000 different probes per 1 $cm^2$, between 100,000 and 500,000 different probes per 1 $cm^2$, or more than 500,000 different (i.e., non-identical) probes per 1 $cm^2$. In a specific embodiment, the microarrays comprise 20,000 to 40,000 probes on a 1×3 inch glass slide.

According to the invention, the microarray is an array (i.e., a matrix) in which each position represents a portion of an organism's genome. For example, each position can contain a DNA or DNA analogue based on genomic DNA to which a particular RNA or cDNA transcribed from that portion of the genome can specifically hybridize. The DNA or DNA analogue can be, e.g., a synthetic oligomer or a gene fragment. In a preferred embodiment, probes based on genomic DNA are "tiled" at sequential sites across an organism's genome. For example, probes based on genomic DNA can be sequentially ordered on a positionally addressable array such that the array comprises at least a portion of the sequence of the organism's genome. The probes can tile across the genomic nucleic acid sequence of any organism. For example, the organism can be a prokaryote or a eukaryote, including but not limited to: bacteria, e.g., *E. coli*; fungi, e.g., Aspergillus, *C. albicans, P. infestans*, or *S. cerevisiae*; Drosophila; *C. elegans*; plants, e.g., a monocot, such as rice, corn, wheat and other grasses, or a dicot, such as beans, Arabidopsis, potatoes or tobacco; animals, such as a domestic animal, e.g. dog, cat, cow, horse, rat, or mouse; a mammal; or a primate, e.g., a human. As will be clear to the skilled artisan, the genome of the organism for which probes are "tiled" in the microarray is preferably used to detect or measure hybridization to RNA (preferably mRNA) or nucleic acid derived therefrom of an organism of the same species.

In a specific embodiment, the sequences of probes tiled at sequential sites contain overlaps, preferably at regular intervals. For example, if overlapping probes A, B, and C are sequentially tiled on the genome so that A is 5' to B and C, and C is 3' to A and B, then a portion of the 5' end of probe B will be identical to the 3' end of probe A, and a portion of the 3' end of probe B will be identical to the 5' end of probe B. FIG. 7A provides an illustration of overlapping probes 703. In another specific embodiment, the sequences of probes tiled at sequential sites are spaced at intervals, preferably regular intervals, across the genome, so that a portion of genomic sequence is skipped between sequential probes. For example, if spaced probes D, E, and F are sequentially tiled on the genome so that D is 5' to E and F, and F is 3' to D and E, then there will be a gap in the genomic sequence between probe D and probe E, and between probe E and probe F. FIG. 7B provides an illustration of spaced probes 713. In yet another embodiment, the sequences of probes tiled at sequential sites are adjacent to one another, so that the probes are neither overlapping, nor spaced. For example, if adjacent probes G, H, and I are sequentially tiled on the genome so that G is 5' to H and I, and I is 3' to G and H, then there will be no gaps in the genomic sequence between probe G and probe H, or between probe H and probe I, and no portion of the sequence of probe H will be identical to either probe or probe I. FIG. 7C provides an illustration of adjacent probes 723.

A skilled artisan will appreciate that highly-overlapping probes will allow for high resolution detection of a relatively smaller portion of the genome, while less overlapping, adjacent, or spaced probes will provide lower resolution detection of a relatively larger portion of the genome. Preferably, probes are tiled so that probes at sequential sites overlap from in a range of from 10–50% of the length of the probe, from 50–90% of the length of the probe, or from 70–80% of the length of the probe. In an alternate embodiment, for highest resolution, probes at sequential sites overlap at all but one base pair. The probes may be of different lengths to normalize binding energies of different oligonucleotides. Shorter probes (15–20 bp) may also provide higher resolution mapping of intron-exon boundaries.

In another specific embodiment, probes may be tiled across a genomic region predicted to contain exons. In still another specific embodiment, probes to known ESTs or predicted exons are included. In a specific embodiment, an array comprises a population of probes, said population comprising a plurality of probes in which each probe corresponds to a predicted or known exon. In a specific embodiment, probes to at least 10,000 or 20,000 known ore predicted probes are included in the population.

5.2.2 Preparing Probes for Microarrays

As noted above, the "probe" to which a particular polynucleotide molecule specifically hybridizes according to the invention contains a complementary genomic polynucleotide sequence. The probes of the exon profiling array preferably consist of nucleotide sequences of no more than 1,000 nucleotides. In some embodiments, the probes of the exon profiling array consist of nucleotide sequences of 10 to 1,000 nucleotides. In a preferred embodiment, the nucleotide sequences of the probes are in the range of 10–200 nucleotides in length and are genomic sequences of a species of organism, such that a plurality of different probes is present, with sequences complementary and thus capable of hybridizing to the genome of such a species of organism, sequentially tiled across all or a portion of such genome. In other specific embodiments, the probes are in the range of 10–30 nucleotides in length, in the range of 10–40 nucleotides in length, in the range of 20–50 nucleotides in length, in the range of 40–80 nucleotides in length, in the range of 50–150 nucleotides in length, in the range of 80–120 nucleotides in length, and most preferably are 60 nucleotides in length.

In a typical example of a genome scanning array of the invention, the probes (e.g., 60-mers) are overlapping by X bp, where X is a selected number, preferably less than 100, 50, or 25 bp, and is for example 5, 8, 10, or 15 bp, or in the range of 5–20 bp. In an another embodiment, a screening array contains adjacent probes, or spaced probes with genomic sequence gaps of, for example, 10, 50, 100, 500, or 1,000 bp between the sequences complementary to sequential probes. A skilled artisan will appreciate that if a genomic sequence for any given probe is an identical distance both 5' and 3' from genomic sequences for two other probes, either of the other probes has a genomic sequence "closest in the genome." In an alternate embodiment, the screening array includes a single probe for each predicted exon in the genome of the organism. In another alternate embodiment, a scanning or screening array is tested under many conditions, and clustering analysis is performed to determine which exons belong to which genes, and to identify regions for further analysis with high-resolution scanning arrays.

In a specific embodiment, once hybridization to expressed nucleic acid has occurred and been detected with a scanning or screening array, indicating the genomic areas of hybridization, a high-resolution scanning array can be used to define more exactly the intron-exon boundaries. This high-resolution array preferably has shorter probes (e.g., in the range of 15–60 nucleotides) than those present in a scanning or screening array, with the sequences of such probes tiled at sequential sites over the region of interest identified as expressed by hybridization to a scanning or screening array, and such tiled probes overlapping to a greater extent than those in a scanning array, and preferably overlapping at all but a single nucleotide.

Depending on the data desired to be obtained, the scanning array, screening array, or high-resolution scanning array can be omitted, and the size and tiling of probes can be designed accordingly. For example, a scanning array can be designed to have sequences tiled at larger intervals to conduct an initial survey of a large genomic region, or smaller intervals to more completely analyze a part of the genome. The highest resolution can be obtained if the oligonucleotides are tiled at single base intervals across the genome. The shortest possible oligonucleotides as probes consistent with obtaining reliable and specific hybridization given the complexity of the genome are desired.

In a specific embodiment, the distance between 5' ends of probes at sequential sites is always less than 500 bp, and more preferably always less than 250 bp, 100 bp, 50 bp, 10 bp, 5 bp, or 2 bp. In another specific embodiment, the genomic sequences for a set of probes on an array span a genomic region of at least 25,000 bp, 50,000 bp, and more preferably at least 75,000 bp, 200,000 bp, 500,000 bp, or 1,000,000 bp.

In another embodiment, at least two of the polynucleotide probes are complementary and hybridizable to intron sequences of at least 10 different genes, and more preferably at least 20 genes, 50 genes, 200 genes, 1000 genes, or substantially all or all of the genes in the genome. In yet another embodiment, at least two of the polynucleotide probes are complementary and hybridizable to sequences contained entirely within an intron.

In an alternate embodiment, the array does not contain one or more matched probes for each of the tiled polynucleotide probes, where the sequence of the matched probes varies only in the identity of a single nucleotide at the same position relative to the tiled polynucleotide probe. For example, where a particular tiled probe has a G residue at the 5th position, the matched probe could have an A, T, or C residue at the fifth position, but otherwise be identical in sequence to the tiled probe. In another alternate embodiment, the array does not contain a number of polynucleotide probes that are not complementary and hybridizable to the genome of the same organism as the tiled probes, where the number of such probes is equal to or greater than the number of tiled probes on the array.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399–5407; McBride et al., 1983, *Tetrahedron Lett.* 24:246–248). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566–568; U.S. Pat. No. 5,539,083).

In a further preferred embodiment, regions of the genome sequence having a low information content are excluded from selection as probes. Examples of sequences having a low information content include, but are not limited to, repetitive elements, simple repeats, and runs of contiguous repetition or "runs" of one base. Contiguous runs of a single base are referred to in the art as "polyX" runs or "polyX" repeats, wherein "X" denotes the nucleotide base (e.g., adenine, thymine, guanine, cytosine, or uracil) that is repeated. Such polynucleotide repeats can be "scored" in a probe sequence, e.g., by simply counting the number of nucleotide bases in the single longest continuous run of any one base or, alternatively, by totaling the cumulative length of bases involved in polyX runs in the probe sequences. PolyX runs can be as short as two bases. However, polyX runs that are more than three, four, five or ten bases in length have particularly low information content and are preferably avoided in oligonucleotide probes of the present invention.

"Simple repeats" refer to tandem repeats of short (e.g., 1–5 bases, more typically 1–3 bases) sequences. By contrast, repetitive elements are longer (e.g., between 20 and 90,000 base pairs, more typically about 1,000 base pairs), more complex sequences that are over-represented in a polynucleotide sample. For example, it is well known in the art that the genomes of many higher organisms, particularly eukaryotes (in particular, higher eukaryotes such as mammals and including humans) contain complex sequences that occur many times and are over-represented in the genome. Typically, these complex repeated elements are specific to the evolutionary lineage of the cell or organism.

Genomic regions containing simple repeats or more complex repetitive elements can be readily identified by the skilled artisan. Such regions can be detected, for example, by sequence comparison to libraries or databases of known elements, or through statistical analysis of new sequence data. In a highly preferred embodiment, a computer program such as RepeatMasker, available on the internet via file transfer protocol at genome.washington. edu/cgi-bin/RepeatMasker, or commercially from Geospiza, Inc. (Seattle, Wash.), is used to compare a polynucleotide sequence of interest to sequences of repetitive elements and/or simple repeats in a database of such sequences. Because such repetitive elements and simple repeats are generally specific to the species of organism from which a polynucleotide sample is derived, preferably the database is a database of repetitive elements and/or simple repeats for an appropriate organism or class of organism (e.g., for primates, rodents, mammals, vertebrates, Arabidopsis, grasses or Drosophila). Typically, such a comparison is done using a "scoring matrix" that can be entered or selected by a user or, alternatively, a default scoring matrix used automatically by the program.

In a preferred embodiment, regions of the nucleotide sequence of interest that align with repetitive element and/or with simple repeat sequences within the database are "masked," e.g., by replacing the aligned bases with "N" or "X" in the program output. A skilled artisan can then select oligonucleotide probes with high information content by selecting oligonucleotide sequences that are complementary to portions of the target sequence that are not masked. Preferably, the selected probes are tiled in regular intervals across the genome with the exception of excluded regions. A skilled artisan will appreciate that regions to be excluded are removed from the sequence used to choose probes prior to applying the tiling strategy for the probes, whether overlapping, spaced, or adjacent. Thus, for example, when a region is excluded, adjacent probes at the boundary of the excluded region may not be adjacent to each other in the complete genomic sequence. Probes are preferably selected using an algorithm that takes into account binding energies, base composition, sequence complexity, cross-hybridization binding energies, and secondary structure (see Friend et al., International Patent Publication WO 01/05935, published Jan. 25, 2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

5.2.3 Attaching Probes to the Solid Surface

The probes are attached to a solid support or surface, which may be made, e.g., from glass, plastic (e.g., polypropylene, nylon), polyacrylamide, nitrocellulose, gel, or other porous or nonporous material. A preferred method for attaching the nucleic acids to a surface is by printing on glass plates, as is described generally by Schena et al, 1995, *Science* 270:467–470. This method is especially useful for preparing microarrays of cDNA (See also, DeRisi et al, 1996, *Nature Genetics* 14:457–460; Shalon et al., 1996, *Genome Res.* 6:639–645; and Schena et al., 1995, *Proc. Natl. Acad. Sci. U.S.A.* 93:10539–11286).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767–773; Pease et al., 1994, *Proc. Natl. Acad. Sci. U.S.A.* 91:5022–5026; Lockhart et al., 1996, *Nature Bio-* technology 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687–690). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, *Nuc. Acids. Res.* 20:1679–1684), may also be used. In principle, and as noted supra, any type of array, for example, dot blots on a nylon hybridization membrane (see Sambrook el al., supra) could be used. However, as will be recognized by those skilled in the art, very small arrays will frequently be preferred because hybridization volumes will be smaller.

In one embodiment, the arrays of the present invention are prepared by synthesizing polynucleotide probes on a support. In such an embodiment, polynucleotide probes are attached to the support covalently at either the 3' or the 5' end of the polynucleotide.

In a particularly preferred embodiment, microarrays of the invention are manufactured by means of an ink jet printing device for oligonucleotide synthesis, e.g., using the methods and systems described by Blanchard in U.S. Pat. No. 6,028,189; Blanchard et al., 1996, *Biosensors and Bioelectronics* 11:687–690; Blanchard, 1998, in *Synthetic DNA Arrays in Genetic Engineering*, Vol. 20, J. K. Setlow, Ed., Plenum Press, New York at pages 111–123. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 cm². The polynucleotide probes are attached to the support covalently at either the 3' or the 5' end of the polynucleotide.

5.2.4 Target Polynucleotide Molecules

The polynucleotide molecules which may be analyzed by the present invention (the "target polynucleotide molecules") may be from any source, but are expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly(A)$^+$ messenger RNA (mRNA) or fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. Nos. 5,545,522, 5,891,636, or 5,716,785). Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). In another embodiment, total RNA is extracted using a silica gel-based column, commercially available examples of which include RNeasy (Qiagen, Valencia, Calif.) and StrataPrep (Stratagene, La Jolla, Calif.). In an alternative embodiment, which is preferred for *S. cerevisiae*, RNA is extracted from cells using phenol and chloroform, as described in Ausubel et al. (Ausubel et al., eds., 1989, *Current Protocols in Molecular Biology*, Vol III, Green Publishing Associates, Inc., John Wiley & Sons, Inc., New York, at pp. 13.12.1–13.12.5). Poly(A)$^+$ RNA can be selected, e.g., by selection with oligo-dT cellulose or, alternatively, by oligo-dT primed reverse transcription of total cellular RNA. In one embodiment, RNA can be fragmented by methods known in the art, e.g., by incubation with $ZnCl_2$, to generate fragments of RNA. In another embodiment, the polynucleotide molecules analyzed by the invention comprise cDNA, or PCR products of amplified RNA or cDNA.

In a preferred embodiment, total RNA, mRNA, or nucleic acids derived therefrom, from a wide number of diverse types of cells of the genome of interest are contacted with the genomic microarrays of the invention, so that all, or substantially all exons in the genome are detected, since different cell types express different RNAs. Cells of interest include, but are by no means limited to, wild-type cells, mutant cells, drug-exposed wild-type cells, drug-exposed mutant cells, primary cells, cell lines, cells of different tissues or developmental stages, modified cells, diseased cells and, in particular, cancer cells. Target polynucleotide molecules that are poorly expressed in particular cells may be enriched using normalization techniques (Bonaldo et al., 1996, *Genome Res.* 6:791–806).

As described above, the target polynucleotides are detectably labeled at one or more nucleotides. Any method known in the art may be used to detectably label the target polynucleotides. Preferably, this labeling incorporates the label uniformly along the length of the RNA, and more preferably, the labeling is carried out at a high degree of efficiency. One embodiment for this labeling uses oligo-dT primed reverse transcription to incorporate the label; however, conventional methods of this method are biased toward generating 3' end fragments. Thus, in a preferred embodiment, random primers (e.g., 9-mers) are used in reverse transcription to uniformly incorporate labeled nucleotides over the full length of the target polynucleotides. Alternatively, random primers may be used in conjunction with PCR methods or T7 promoter-based in vitro transcription methods in order to amplify the target polynucleotides.

In a preferred embodiment, the detectable label is a luminescent label. For example, fluorescent labels, bio-luminescent labels, chemi-luminescent labels, and calorimetric labels may be used in the present invention. In a highly preferred embodiment, the label is a fluorescent label, such as a fluorescein, a phosphor, a rhodamine, or a polymethine dye derivative. Examples of commercially available fluorescent labels include, for example, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.). In another embodiment, the detectable label is a radiolabeled nucleotide.

In a further preferred embodiment, target polynucleotide molecules from two or more different sources are distinguishably labeled, such as with different color labels. In a highly preferred embodiment, these different sources are chosen so as to maximize the differential expression of genes of interest. The skilled artisan will appreciate that differentially expressed exons are easier to detect in this manner. For example, target polynucleotide molecules can be isolated from diverse tissues or growth conditions and distinguishably labeled with different color labels for each source of molecules. In some embodiments of the invention, at least 2, 5, 10, 20, or 100 dyes of different colors can be used for labeling.

In one embodiment, such diverse conditions can be determined using a large collection of known genes and examining the correlation of their expression in pairwise combinations of experimental conditions. For example, the correlation data may be based on expression data from at least 2, 5, 10, 100, 500, 2,000, 10,000, or 50,000 different conditions. Conditions of interest include, but are by no means limited to, wild-type cells, mutant cells, drug-exposed wild-type cells, drug-exposed mutant cells, primary cells, cell lines, cells of different tissues or developmental stages, modified cells, diseased cells and, in particular, cancer cells. The correlation data are used to assemble clusters of related conditions (Ross et al., Nature Genet. 24, 227–35, 2000; Friend et al., International Patent Publication WO 00/24936, published May 4, 2000) and the most informative members of each cluster are used in subsequent steps. Informative conditions may be picked via the intensity of the observed profile of the experimental condition compared to the profile of a reference condition in a two color assay with the expressed nucleic acids from the reference condition labeled with a first fluorescent dye, and the expressed nucleic acids from the experimental condition labeled with a second, distinguishable fluorescent dye. Alternatively, a single color assay can be performed using the appropriate normalization controls, and the ratios of all possible combinations can be generated using a computer.

5.2.5 Hybridization to Microarrays

Nucleic acid hybridization and wash conditions are chosen so that the target polynucleotide molecules specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. Typical hybridization conditions for the cDNA microarrays of Schena et al. are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B.V.; and Kricka, 1992, Nonisotopic DNA Probe Techniques, Academic Press, San Diego, Calif.

Particularly preferred hybridization conditions for use with the scanning, screening and/or high-resolution scanning arrays of the present invention include hybridization at a temperature at or near the mean melting temperature of the probes (e.g., within 5° C., more preferably within 2° C.) in 1 M NaCl, 50 mM MES buffer (pH 6.5), 0.5% sodium sarcosine and 30% formamide.

5.2.6 Signal Detection and Data Analysis

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not expressed in the cell will have little or no signal (e.g., fluorescent signal), and a gene for which the encoded mRNA is prevalent will have a relatively strong signal.

In one embodiment, positive signals due to nonspecific hybridization or background are eliminated prior to further analysis. For example, positive signals from regions of the genome sequence having a low information content (e.g., repetitive elements, simple repeats, or polyX repeats) can be eliminated from further analysis. In another embodiment, a quality score is created for each probe based on such a computer analysis; this quality score can be multiplied by the signal intensity for that particular probe to generate data that effectively eliminates nonspecific positive signals. In yet another embodiment, any positive signal where only a single oligonucleotide in a genomic region yields a significant signal may also be eliminated, since it is unlikely to correspond to a true exon.

In another embodiment, multiple conditions (e.g., tissue types, developmental stages, drug treatments, disease states, or cell culture growth conditions) can be used to distinguish between signal due to exons and signal due to background. As shown in FIGS. 4A and 4B, background signal usually remains relatively constant for each condition, while expression of the exons is markedly different. Thus, by comparing data from two or more conditions, more accurate distinctions between signal due to exons and signal due to background can be made. Preferably, when hybridization data is obtained from two different conditions, as illustrated in FIGS. 4A and 4B, a difference statistic is generated that minimizes the effects of measurement errors and background. Thus, the filtered data tends to show the presence of exons more clearly. A preferred form of this difference statistic is described in Stoughton et al., International Patent Publication WO 00/39339, published Jul. 6, 2000. This embodiment of the present invention is also particularly well suited to implementation using two-color fluorescent labeling and hybridization protocols.

In another embodiment of the invention, pairwise difference statistics are generated from the hybridization data obtained from the two different conditions for each possible pair. Alternatively, covariance methods may be applied to the entire set of conditions. (See, e.g., Mardia et al., Multivariate Analysis, Academic Press, London, 1979; Comon, P, 1994, *Signal Processing* 36:287–314; Te-Won Lee, Independent Component Analysis: Theory and Applications, Kluwer Academic Publishers, 1998.) For example, the principal mode of variation of the tiling probe intensities across conditions will correspond to the exon pattern.

In other specific embodiments, positive signals can be distinguished from background noise or cross-hybridization with related sequences by absolute signal, change in signal with change in growth condition, or comparison of the signal to that obtained with oligonucleotides representing the complementary strand. This latter embodiment makes use of hybridization data that are obtained from hybridization probes complementary to the reverse complement strand to filter the hybridization signals obtained from the hybridization probes that are complementary to the mRNA coding strand ("Complementary Strand Filtering Method").

In addition to probes complementary to the reverse complement strand, the method can use comparisons of the signal from the forward strand to that obtained from a reverse or complementary strand. For example, where a sequence in the forward strand is 5'-ATACG-3', and the reverse complement sequence is 5'-CGTAT-3', the reverse sequence is 5'-GCATA-3' and the complement sequence is 5'-TATGC-3'. Furthermore, one can switch local AT and/or GC pairs, or use a random permutation of the forward sequence. For example, where a sequence in the forward strand is 5'-ATACG-3', one could switch GC pairs to obtain 5'-ATAGC-3', switch AT pairs to obtain 5'-TATCG-3', or use a random permutation to obtain 5'-CATGA-3' in order to generate a comparison strand to control for signals arising from nonspecific hybridization, depending upon what criteria are important for control probe selection. For example, one can preserve the %GC of the forward probe using a reverse complement, reverse or complement probe, as shown in Table 1. The probe sequence at the proximal end of the probe (i.e., that end attached to the array) is less accessible for hybridization than the distal end. As shown in Table 1, where preservation of the positioning of, for example, GC or AT-rich regions is important, the complement probe can be used. Preservation of the percent A, C, G and T in the forward probe can be accomplished by using a reverse probe or a randomly permuted probe. Also as shown in Table 1, the reverse complement probe is the only probe for which a single-strand labeling protocol is necessary. Some amplification methods, such as the generation of cDNA from mRNA, create a reverse complement to the forward sequence; if both strands of the cDNA are labeled, the sample will hybridize detectably to both the forward probe and reverse complement probe, unless only the sample strands that hybridize to the forward probe are labeled.

For carrying out this Complementary Strand Filtering Method, it is preferred that the sample preparation protocol provides a single stranded nucleic acid sample that is specific to the mRNA coding sequence (e.g., the protocol in Section 6, Example 1 herein); for example, a protocol that results in the production of a hybridization sample that has a relatively low abundance of molecules that will hybridize to the tiling probes that are complementary to the reverse complements of expressed sequences. Additionally, it is highly preferred that coding regions rarely occur in overlapping regions of the forward and reverse DNA strands of the DNA sequence represented on the screening array.

According to the Complementary Strand Filtering Method, high coding probabilities are assigned to regions of one strand of the tiled DNA that hybridize with significantly higher intensities to array probes complementary to one strand vs. the other.

It is known that the abundance and distribution of the bases G and C within a probe correlate to its "stickiness" or potential for cross hybridization. Since G and C bases are complementary to C and G bases, respectively, the relevant properties contributing to cross-hybridization are expected to be conserved between the complement and the reverse complement of a sequence. Hence, evidence of cross-hybridization is supplied by detecting significant hybridization to the reverse complement probes of the scanning or screening array. It will be readily apparent to the skilled artisan that the Complementary Strand Filtering Method is less preferred for coding regions that contain GC-rich regions, or AT-rich regions, due to the increased cross-hybridization in such coding regions. Additionally, cross-hybridization to sequences having low information content can also be filtered using the Complementary Strand Filtering Method, since the reverse complement of a sequence having low information content is also likely to have low information content.

The comparison of one strand to its complement is preferably made when probes complementary to both strands are printed adjacent to each other on the array. This offers direct strand comparison without the need for renormalization techniques due to technological or biological factors.

In a specific embodiment of the invention, the Complementary Strand Filtering Method proceeds as follows:

Complementary Strand Filtering Method

Let $x_i$ represent the log intensity of the $i^{th}$ probe on the strand for which putative exon discovery is desired (strand A). Let $y_i$ represent the log intensity of the $i^{th}$ complementary probe on the opposite strand (strand B). Intensity normalization and detrending have preferably already been performed.

TABLE 1

| | Control Probes* | | | | | |
|---|---|---|---|---|---|---|
| Example | Reverse 5'-gcata-3' | Complement 5'-tatgc-3' | Reverse Complement 5'-cgtat-3' | Switch G & C 5'-atagc-3' | Switch A & T 5'-tatcg-3' | Random Permutation 5'-catga-3' |
| Preserve % GC | Y | Y | Y | Y | Y | N |
| Preserve GC trend | N | Y | N | Y | Y | N |
| Preserve individual A,C,T,G % | Y | N | N | N | N | Y |
| Need single strand labeling protocol | N | N | Y | N | N | N |

*Forward probe = 5'-atacg-3'.
Y: Control probe will satisfy this Example situation.
N: Control probe will not satisfy this Example situation.

(1) Choose a windowing function, such as rectangular, Hamming, etc. and a windowing width. In practice, the width of the window relates to the spacing of the probes as well as the expected length of an exon. Let $x_i^w$ and $y_i^w$ be the windowed versions of $x_i$ and $y_i$.

(2) Choose a method for comparing $x_i^w$ to $y_i^w$ and assigning a new intensity $\widehat{x_i}$ to probe i in strand A. Examples of methods that maybe used include one or more of the following alternative methods:

(a) Choose a difference threshold d, then $\widehat{x_i} = x_i^w$ if mean $(x_i^w)$−mean$(y_i^w)$>d, otherwise $\widehat{x_i} = 0$. In practice, since log intensities are being dealt with, d is selected to represent an order of magnitude difference in expression that is deemed significant such as one.

(b) Choose a ratio threshold r, then $\widehat{x_i} = x_i^w$ if mean$(x_i^w)$/mean$(y_i^w)$>r, otherwise $\hat{x}_i = 0$. In practice, r is selected to represent a ratio difference in expression that is deemed significant, such as two.

(c) Choose a method for correlating two signals$(x_i^w, y_i^w)$ and modify the intensity based upon this score. For example, f could represent the dot product between these two signals and $\widehat{x_i} = (e^{-x_i^w \cdot y_i^w}) x_i^w$. In this case, since $x_i^w$ and $y_i^w$ are posidtive signals. the more signals, the more similar they are, the smaller the value of the modified signal $\widehat{x_i}$.

(3) Steps 1 and 2 are applied to each probe on strand A, then to each probe on the complementary strand B. A post-processing filter is then preferably applied to remove noise. For example, a running mean or median filter can be used. Preferably, the width of this filter is chosen to be smaller than the width of an exon.

Example 3 demonstrates that the Complementary Strand Filtering Method with the difference algorithm (2)(a) can be used in the analysis of scanning or screening array hybridization data to reduce the number of false positive hybridization signals, thereby allowing accurate identification of the known exons of the human Retinoblastoma (Rb) gene.

In another embodiment, filtering of cross-hybridization signals can be accomplished by performing searches for known expressed sequences that would be likely to hybridize to any probe (e.g., based on predicted duplex binding energies, blastn comparisons, etc.). Those probes with perfect or near-perfect matches (more preferably, high duplex binding energy) to expressed regions other than the one being reported are given a low confidence when declaring exons. Since this method focuses on near-sequence-neighbor events, it is a good partner to the Complementary Strand Filtering Method (see Example 3), which deals with cross-hybridization from a large diffuse pool of low information content sequences.

Particularly preferred embodiments use a combination of the techniques discussed herein to filter out false positive signals from the scanning or screening array probes and reveal the actual exon locations. For example, individual biological conditions are profiled with probes for both strands, the Complementary Strand Filtering Method is used to reduce false signals, blastn and duplex energy calculations are performed to filter out close-neighbor cross-hybridization events, then multiple conditions are intercompared to find exon regions that may be expressed only in some cell conditions.

In a further embodiment, regions of the genome containing continuous areas of positive signal are noted for additional analysis to confirm exons. Such regions may be analyzed by, for example, searching the genetic sequence for coding regions or splicing signals, correlation with a database containing EST locations, or comparison with lists of known genes in the same or, alternatively, other species of organism to identify regions of homology or previously undetected genes. Methods for rapid detection of nearly identical sequences such as blastn (Altschul et al., 1990, *J. Mol. Biol* 215:403–10) are also well-suited to this step. In another embodiment, false positive and false negative rates can be determined for each probe. In a highly preferred embodiment, the probability that a particular nucleotide in the region of interest is expressed can be calculated using all available information regarding that region.

In a preferred embodiment, cDNAs from two different cells are hybridized to the binding sites of the microarray. The cDNA derived from each of the two cell types are differently labeled so that they can be distinguished. For example, in the case of drug responses, one cell is exposed to a drug and another cell of the same type is not exposed to the drug. In one embodiment, for example, cDNA from a cell treated with a drug is synthesized using a Cy3-labeled dNTP, and cDNA from a second cell, not drug-exposed, is synthesized using a Cy5-labeled dNTP. When the two cDNAs are mixed and hybridized to the microarray, the relative intensity of signal from each cDNA set is determined for each site on the array, and any relative difference in abundance of a particular mRNA is thereby detected.

In the example described above, the cDNA from the drug-treated cell will fluoresce green when the fluorophore is stimulated, and the cDNA from the untreated cell will fluoresce red. As a result, when the drug treatment has no effect, either directly or indirectly, on the relative abundance of a particular mRNA in a cell, the mRNA will be equally prevalent in both cells, and, upon reverse transcription, red-labeled and green-labeled cDNA will be equally prevalent. When hybridized to the microarray, the binding site(s) for that species of RNA will emit wavelength characteristic of both fluorophores. In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, *Science* 270:467–470. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. For example, the absolute amount of a particular mRNA in a drug-treated or diseased cell state or first tissue type can be compared to that of an untreated or normal cell state or tissue type. However, it will be recognized that it is possible to use cDNA from a single cell state or second tissue type.

When fluorescently labeled probes are used, the fluorescence emissions at each site of a transcript array can be, preferably, detected by scanning confocal laser microscopy. In one embodiment, a separate scan, using the appropriate excitation line, is canted out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639–645). In a preferred embodiment, the arrays are scanned with a laser fluorescent scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639–645. Alternatively, the fiber-optic bundle described by Ferguson et al, 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

5.2.7 Determination of Gene Structure

Figure 1:
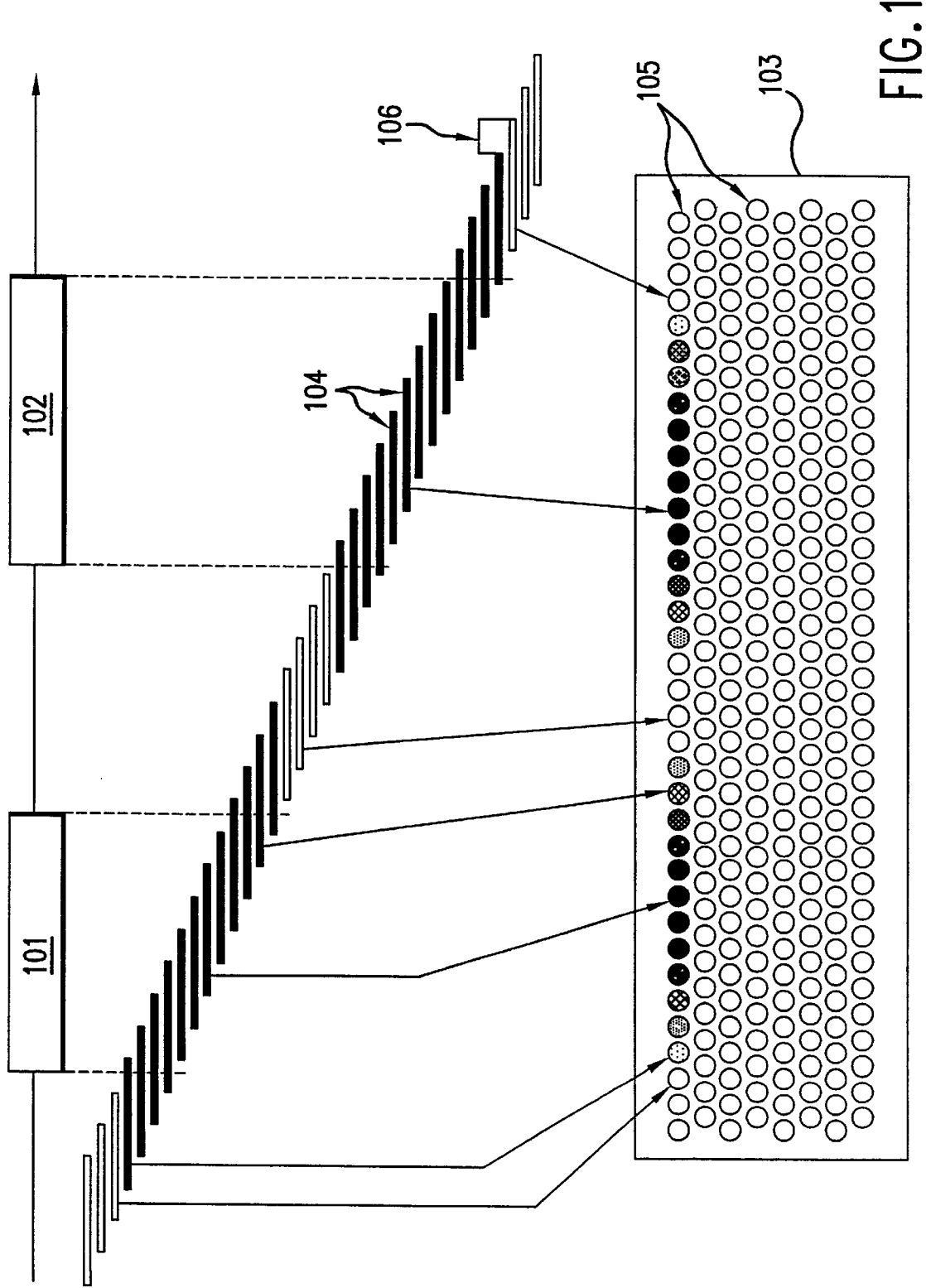

Positive signals can be used to determine gene structure in several ways. In one embodiment, a screening or scanning array is used to identify or verify the locations of expressed exons. In another embodiment, a high-resolution scanning array is used to examine areas of transition from positive to negative signals to determine the intron-exon boundaries. As illustrated in FIG. 1, probes that only partially overlap an exon will result in lower signals than probes which are entirely within the sequence of an exon. Thus, as the sequence of the probe moves across the intron-exon boundary from being totally within an intron to totally within an exon, the hybridization signal to an mRNA encoded by that exon will show a gradual transition from no signal to positive signal. As will be appreciated by one of skill in the art, smaller steps between probes on the array will allow for greater resolution of this intron-exon boundary transition. In a further embodiment, the length and free energy of binding for the region of overlap can be calculated, and used in combination with the positive signal to determine the precise intron-exon boundary. In a still further embodiment, probe behavior is distinctly different as the probes enter and leave exons; this information can be modeled and used to identify intron-exon boundaries.

In one embodiment, a method is provided for determining the probability that an individual nucleotide within the genome of a species of organism is expressed in response to a condition, comprising (a) contacting a first sample and a second sample, both comprising RNAs or nucleic acids derived therefrom from one or more cells of said species of organism, with an array under conditions conducive to hybridization, said array comprising a positionally-addressable ordered array of polynucleotide probes bound to a solid support, said polynucleotide probes comprising a plurality of at least 100 polynucleotide probes of different nucleotide sequences, each said different nucleotide sequence comprising a sequence complementary and hybridizable to a different genomic sequence of the same species of organism, said respective genomic sequences for the probes being found at sequential sites in said genome of said species of organism, said contacting being under conditions conducive to hybridization between said RNAs or nucleic acids derived therefrom and said probes, said first sample being derived from cells exposed to a condition, said second sample being derived from cells not exposed to said condition, said RNAs or nucleic acids derived therefrom from said first and second samples being differentially labeled; (b) determining, for each probe in said plurality, whether or not hybridization of one or more of said RNAs or nucleic acids derived therefrom from said first or second samples occurs; and (c) based on the determinations in step (b), calculating the probability that a given nucleotide within said respective genomic sequences is expressed in response to a condition.

In another embodiment, the exact intron-exon boundary can be established by examination of the nucleotides at the suspected junctions and using known rules for message splicing (Oshima and Gotoh, 1987, *J. Mol. Biol.* 195:247–59). For example, it is well-understood that introns typically begin with the dinucleotide GT and end with the dinucleotide AG, and that a "branch site" element is usually located at the 3' end of an intron. Thus, the sequence of a region identified as an intron-exon boundary may be examined for one of these features, so that the exact boundary of the exon can be determined (Zhang, 1998, *Hum. Mol. Genet.* 7:919–32). Thus, hybridizarion data from the genomic scanning arrays can be used to narrow the search window for exon prediction programs. In yet another embodiment, the intron-exon boundary information generated by the present invention can be used to directly calculate novel rules for message splicing. In still another embodiment, hybridization data from the genomic scanning or screening arrays can be used to identify trans-splicing or duplication events, multiple promoter elements, alternate 3' RNA processing, and RNA editing (see, e.g., Yamanaka et al., 1997, *Proc. Natl. Acad. Sci. USA* 94:6462–7; Caudevilla et al., 1998, *Proc. Natl. Acad. Sci. USA* 95:12185-90; Koenigsberger et al., 2000, *Proc. Natl. Acad. Sci. USA* 97:2291–96).

In another embodiment, the structure of a gene can be confirmed by using the array data to design primers for PCR. For example, primers can be designed for each predicted exon; such primers can be used to ensure that the predicted gene structure is accurate by, for example, using the primers as forward and reverse primers in PCR to determine if the primers amplify a fragment. The fragment can also be tested to see if it has the predicted length or sequence. For example, one can amplify the sequence between the primers, sequence the amplified product, and compare the actual sequence to the predicted gene structure. FIG. 12 illustrates an exemplary embodiment of the use of array data to design primers for PCR to confirm that an previously-unknown exon identified by the methods of the present invention is a part of a gene encoding a known EST by using a primer that is complementary to the EST and a primer that is complementary to the previously-unknown exon to generate a transcript that contains both EST sequence and the sequence from the previously-unknown exon.

In a specific embodiment, scanning or screening arrays can be used to extend known sequence. This is accomplished by designing two PCR primers. The first primer is derived from the sequence of a known EST. The second primer is derived from the sequence of an exon that the scanning or screening array shows to be co-regulated with the exon producing the EST. If the EST and exon are contained within the same mRNA, RT-PCR of that mRNA will produce cDNA containing both. Those of skill in the art will recognize that this approach can be used to determine sequence both upstream and downstream of a particular EST. Furthermore, it will be apparent that the co-regulated unknown sequence can be a noncoding region such as a 5' noncoding region or a 3' noncoding region, as well as an exon.

In a further embodiment, expression data from multiple conditions from a given genomic sequence are used to determine which sequences are likely to be parts of the same gene based on coordinate control (Ross et al., 2000, *Nature Genet.* 24:227; Friend et al., International Patent Publication WO 00/24936, published May 4, 2000). In a still further embodiment, clustering data can be used to determine which exons belong to which genes across a linear genomic region. For example, if exons appear to be co-regulated based on clustering data and are within a given linear region of genomic DNA of one another, e.g. 1 megabase, it is likely that these exons are within the same gene. However, if exons appear to be co-regulated based on clustering data, but are neither adjacent in the genome, nor within a given linear region of genomic DNA of one another, e.g. 1 megabase, it is unlikely that these exons are within the same gene.

In a further embodiment, screening arrays can be used to determine whether particular exons are present within a single mRNA transcript. A plurality of samples is contacted with a positionally-addressable array containing probes that are identified as complementary and hybridizable to exons in the genome of a species of organism, where the samples each comprise RNAs or nucleotides derived therefrom from a cells exposed to a condition and RNAs or nucleotides derived therefrom from a cell of said species of organism exposed to a different condition, and where the RNAs or nucleotides derived therefrom being differentially labeled between conditions. The level of hybridization to a first potential exon and the level of hybridization to a potential neighboring exon are correlated over the plurality of samples. These exons constitute "seed" exons. The expression of other neighboring exons is then correlated with the expression of the seed exons, until no more exons can be correlated. The exons thus correlated are present on a single mRNA transcript.

In a more specific embodiment, the method of determining whether respective sequences encoded by two or more exons are indicated to be present in a single mRNA transcript, comprises (a) contacting, under conditions conducive to hybridization, a plurality of samples with a positionally-addressable array containing probes that are identified as complementary and hybridizable to potential exons in the genome of a species of organism, said samples each comprising RNAs or nucleic acids derived therefrom from a cell of said species of organism exposed to a different condition; and (b) determining whether the level of hybridization to one or more probes complementary and hybridizable to RNA or nucleic acids derived therefrom encoded by a first potential exon and the level of hybridization of one or more probes complementary and hybridizable to RNA or nucleic acids derived therefrom encoded by a potential neighboring exon are correlated over the plurality of samples, wherein if said levels are correlated, said respective sequences encoded by said first potential exon and said neighboring exon are indicated to be present in a single RNA transcript. This method can be further extended to additional exons by (c) determining whether the level of hybridization to one or more probes complementary and hybridizable to RNA or nucleic acids derived therefrom encoded by an exon additional to said first exon and said neighboring exon, and the respective levels of hybridization of one or more probes complementary and hybridizable to RNA or nucleic acids derived therefrom encoded by said first exon and said neighboring exon, are correlated over a plurality of samples, wherein if said levels are correlated, said respective sequences encoded by said first potential exon, said neighboring exon and said additional exon are indicated to be present in said single RNA transcript; and (d) repeating step (c) until no further exons are indicated to be present in said single RNA transcript.

In another embodiment, a method is provided for verifying predicted exons in the genome of an organism, comprising (a) identifying expressed exons, said identifying being accomplished by contacting under conditions conducive to hybridization a first sample and a second sample with a positionally-addressable ordered array of polynucleotide probes bound to a solid support, said polynucleotide probes comprising a plurality of at least 100 polynucleotide probes of different nucleotide sequences, each said different nucleotide sequence comprising a sequence complementary and hybridizable to a different genomic sequence of said genome, said respective genomic sequences for the probes being found at sequential sites in said genome, said first sample and second sample comprising RNA or nucleic acids derived therefrom obtained from cells exposed to different respective conditions; and (b) determining whether an expressed exon identified in step (a) corresponds to a predicted exon in said genome, and, if so, thereby verifying the predicted exon.

In a particular embodiment of the claimed invention, the amino terminus of a protein is determined by identifying the nearest start codon on the 5' end of the predicted transcript. In a preferred embodiment, the amino terminus of a protein is determined by identifying an area (e.g. as within an identified sequence of 10 or 5 nucleotides) of transition from a negative signal to a positive signal. Preferably, this transition represents the first exon in a group of coordinately regulated exons. The amino-terminus of an encoded protein is then located by identifying the nearest start codon 3' to such a transition area for which an internal ribosome entry site (IRES) appears in between the transition area and the start codon. An IRES is a complex nucleotide sequence where ribosomes bind in a cap-independent fashion and start translation at the next AUG codon downstream. See, e.g., Molecular Biology of the Cell, 3d ed., 1994, Alberts, B. et al., p. 462.

In an optional step, predicted intron-exon boundaries may be tested by use of PCR amplification of cDNA derived from mRNA using primer(s) that overlap the predicted intron-exon junction(s). Thus, only if the predicted splicing occurs, resulting in the mRNA and thus cDNA of predicted sequence, will the primer overlapping that junction have the correct sequence, and thus greatest amplification efficiency in producing the amplified segment of predicted length. In a preferred embodiment, a set of different primers (e.g. 3, 5, or 8 primers) can be individually tested (with a second primer) for their ability to prime amplification across a predicted intron-exon junction, each primer having a sequence across a predicted splicing junction.

As further confirmation, if desired, the RNA transcript may be cloned and sequenced. The data generated by genomic tiling experiments of the invention dramatically accelerates this process by providing enough information to design the primers that can be used to amplify the gene using, e.g., reverse-transcriptase polymerase chain reaction (RT-PCR).

5.3 Implementation Systems and Methods

The analytical methods of the invention can preferably be implemented using a computer system, such as the computer system described in this section, according to the following programs and methods. Such a computer system can also preferably store and manipulate the genomic sequences of the present invention, including the sequences of the polynucleotide probes, preferably further identifying the positional location of each probe on the array, such that these sequences can be used by a computer system or computer program product in implementing the analytical methods of this invention. Accordingly, such computer systems and computer program products are also considered part of the present invention.

An exemplary computer system suitable for implementing the analytic methods of this invention is illustrated in FIG. 6. Computer system 601 is illustrated here as comprising internal components and as being linked to external components. The internal components of this computer system include a processor element 602 interconnected with a main memory 603. For example, computer system 601 can be an Intel Pentium®-based processor of 200 MHZ or greater clock rate and with 32 MB or more main memory. In a preferred embodiment, computer system 601 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 604. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device 605, which is most typically a monitor and a keyboard together with a graphical input device 606 such as a "mouse" or a "trackball." The computer system is also typically linked to a network link 607 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 6. The software components comprise both software components that are standard in the art and components that are special to the present invention. These software components are typically stored on mass storage such as the hard drive 604, but can be stored on other computer readable media as well including, for example, one or more floppy disks, one or more CD-ROMs, one or more DVDs or one or more DATs. Software component 610 represents an operating system which is responsible for managing the computer system and its network interconnections. The operating system can be, for example, of the Microsoft Windows™ family such as Windows 95, Windows 98, Windows NT, Windows 2000, or Windows Millennium. Alternatively, the operating software can be a Macintosh operating system, a UNIX operating system or the LINUX operating system. Software components 611 comprises common languages and functions that are preferably present in the system to assist programs implementing methods specific to the present invention. Languages that can be used to program the analytic methods of the invention include, for example, UNIX or LINUX shell command languages such as C and C++, PERL, FORTRAN, HTML and JAVA. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 612 comprises analytic methods of the present invention, preferably programmed in a procedural language or symbolic package. For example, software component 612 preferably includes programs that cause the processor to implement steps of accepting a plurality of gene sequences, such as the nucleotide sequence of the genome of the species of organism used for the array, or the nucleotide sequences of the probes used on the array, preferably in conjunction with the positional location of the probes on the array, and storing the gene sequences, and alternatively, positional locations, in the memory. For example, the computer system can accept gene sequences that are manually entered by a user (e.g., by means of the user interface). More preferably, however, the programs cause the computer system to retrieve gene sequences from a database or compendium of gene sequences. Such gene sequences can be stored on a mass storage (e.g., a hard drive) or other computer readable medium and loaded into the memory of the computer, or the gene sequences can be accessed by the computer system by means of the network 607. In one embodiment, the computer system or computer program product receives hybridization signal data from the analysis of the array, e.g., from a scanner analyzing the array. In an alternative embodiment, the computer system or computer program product receives hybridization signal data through direct user input.

The computer system or computer program product can then be used to carry out the analytical methods of the invention. For example, the computer system or computer program product can be used to identify or verify the locations of expressed exons, or to determine the intron-exon boundaries in the genome of interest. Once the analytical methods of the invention have been carried out, the results are output, e.g., by displaying on a computer screen, by printing a copy of the results on a printer, by saving the results to a file on a storage device or on removable media, or by transmitting the results over a computer network, such as the Internet.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

6. EXAMPLES

The following examples are presented by way of illustration of the previously described invention, and are not limiting of that description in any way. In particular, the examples presented herein below describe the analysis of the human CXCR-4 gene.

Example 1

Figure 2:
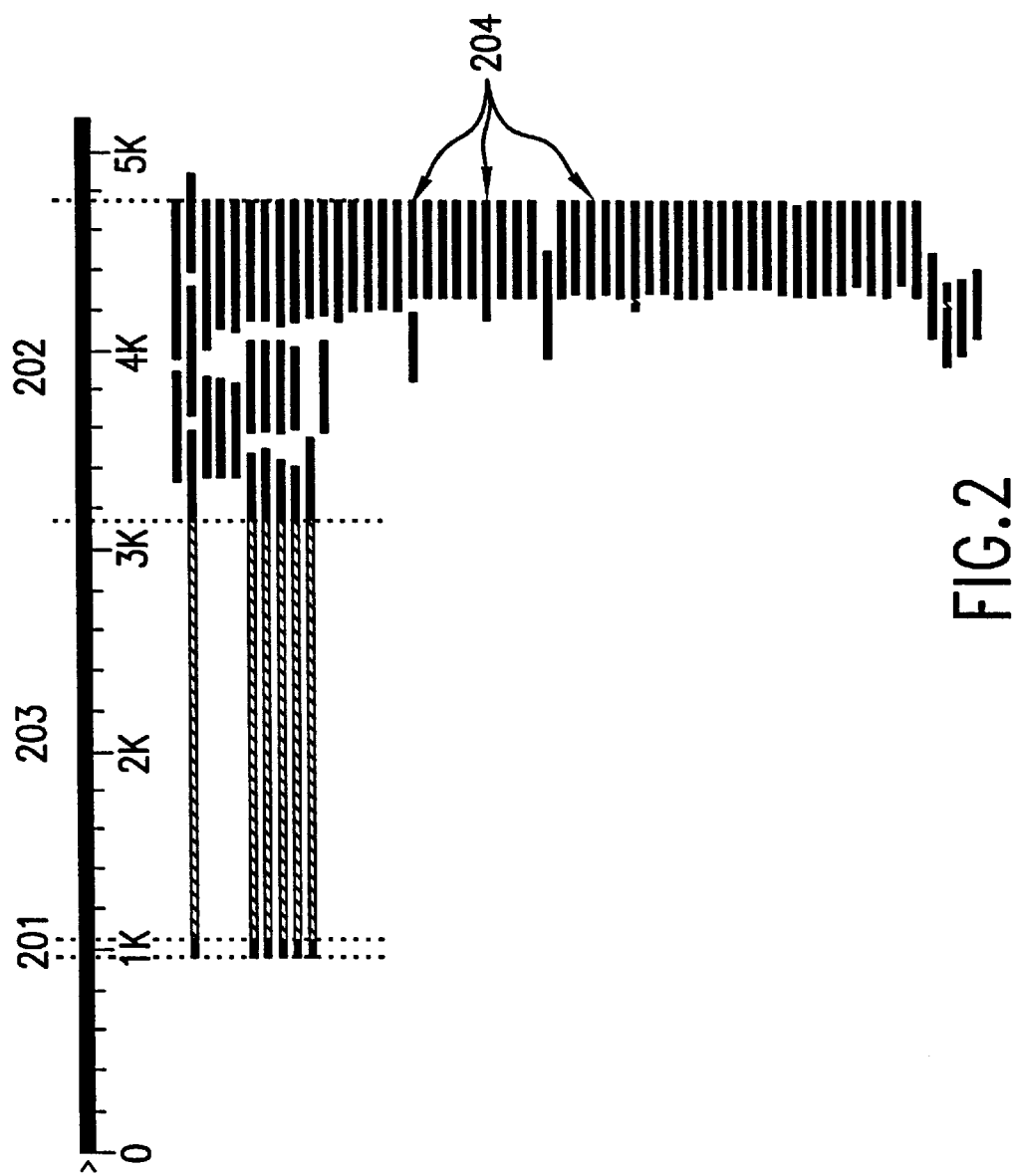

The 5161 bp region of human chromosome 2 that contains the chemokine receptor gene CXCR4 was analyzed using the methods of the invention. The genomic organization of the CXCR-4 gene has been extensively studied, and it is known that the gene contains 2 exons of 103 and 1563 bp interrupted by a single 2132 bp intron (Wegner et al., 1998, *J. Biol. Chem.* 273:4754–60). FIG. 2 shows the position of the two exons by mapping ESTs onto the genomic sequence of the CXCR-4 gene.

A tiled genome array was generated in two steps. First, the 5161 bp region from human chromosome 2 (Genbank Accession Number Af005058) was parsed into a list of 5101 60-mers for probe selection. This list of possible probes was analyzed by the RepeatMasker computer program, which identified 110 of the potential probes as containing regions of low information content (e.g., repetitive elements, simple repeats, or polyX repeats); these 110 sequences were eliminated from further analysis. Second, a high-density oligonucleotide array was synthesized containing the remaining sequences tiled in 5 bp steps. Specifically, the array contained 910 different 60-mers that tiled through the entire 5161 bp region containing the CXCR-4 gene. The array was synthesized on a 1×3 inch glass slide using inkjet technology developed by Rosetta Inpharmatics (Blanchard, International Patent Publication WO 98/41531, published Sep. 24, 1998). The reverse complements for each of the different 60-mers were also synthesized on the array to the right of the primary 60-mers to serve as negative controls. Probes designed to analyze the genomic structure of other genes in the human genome were synthesized on the remainder of the array, resulting in an array with approximately 25,000 60-mer probes.

Target polynucleotides were obtained by preparing total RNA from two cell lines, a human T lymphocyte cell line (Jurkat, ATCC #TIB-152) and a chronic myelogenous leukemia cell line (K562, ATCC #CCL-243), as described previously (Marton et al., 1998, *Nat. Med.* 4:1293–1301). Poly-A+ RNA (mRNA) was isolated from each cell line and labeled using reverse transcription primed with a mixture of random 9-mers and d(T)-20 primers. Specifically, 1.5 µg of mRNA was mixed with 1.5 µg of random 9-mers and 1.5 µg of d(T)-20, and the mixture was incubated for 10 minutes at 70° C., 10 minutes at 4° C., and 10 minutes at 22° C. To this mixture was added 0.5 mM amino-allyl-dUTP (Sigma A-0410), 0.5 mM dNTP, 1×RT buffer, 5 mM $MgCl_2$, 10 mM DTT, and 200 units Superscript (GibcoBRL), bringing the final reverse transcription reaction volume to 100 µl. This reverse transcription reaction was incubated for 10 minutes at 42° C., then the RNA was hydrolyzed by adding 20 µl EDTA+NaOH and incubating at 65° C. for 20 minutes. The reaction was neutralized by adding 20 µl of 1 M Tris-HCl pH 7.6. The resulting amino-allyl labeled single-stranded cDNA was purified using a Microcon-30 (Millipore, Bedford, Mass.). The purified cDNA resulting from the Jurkat cells was coupled to Cy3 dye using a Cy Dye™ kit (Amersham Pharnacia, Piscataway, N.J., #Q15108), while the purified cDNA resulting from the K562 cells was coupled to Cy5 dye in the same manner.

Figure 3:
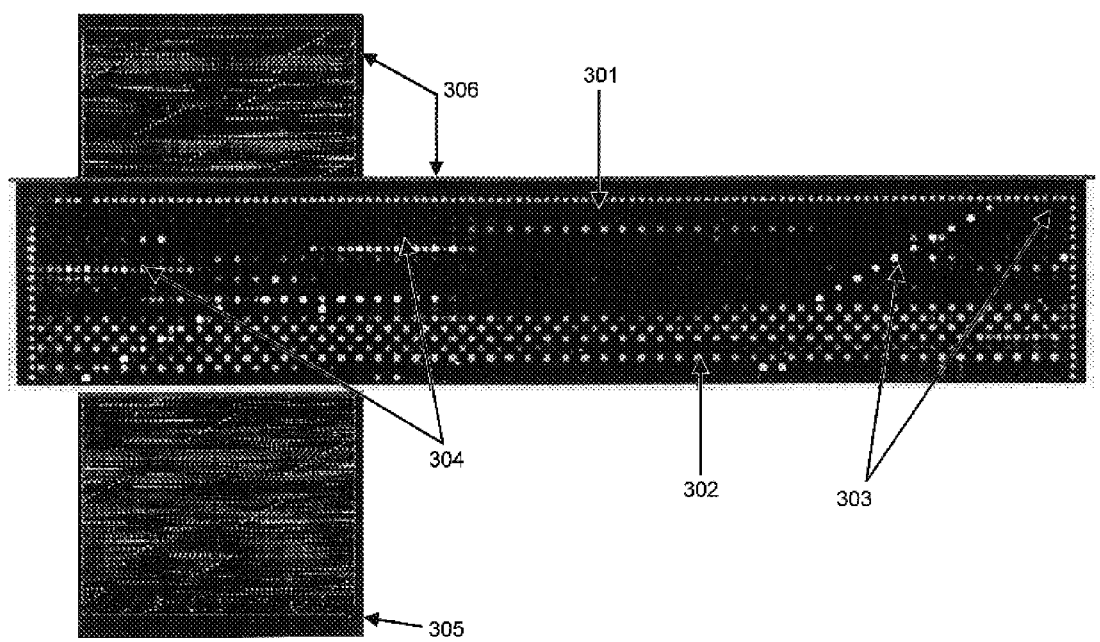

Prior to analysis on the array, the cDNA samples were combined and added to 3 ml of hybridization solution, consisting of 1 M NaCl, 50 mM MES (pH 6.4), 0.50% Sarcosine, and 30% formamide. The combined samples in hybridization solution were then placed in a plastic bag with the array and incubated for 12 hours at 42° C. on a rotisserie to allow the labeled target polynucleotides to hybridize to the array. Following the hybridization step, the array was washed for 20 seconds at room temperature in a beaker containing 50 ml of the hybridization solution, followed by an additional 20 second wash in a low salt buffer (10 mM NaCl, 50 mM MES (pH 6.4), and 0.005% Sarcosine), then scanned using a GMS 418 scanner (Genetic Microsystems). FIG. 3 shows the scanned image of the array; the 960 sequences corresponding to the CXCR-4 gene are located on the top portion of the array.

FIG. 4 shows a quantitative analysis of the hybridization data for the CXCR-4 gene from this array. FIGS. 4A and 4B show the log intensity for each of the 910 60-mers tiled through the genomic region for the K562 and Jurkat samples respectively. This data shows that the CXCR-4 gene is highly expressed in Jurkat cells but not in K562 cells. FIG. 4C shows an error weighted ratio of the signal intensities from the two conditions. The ratio clearly shows the position of the two exons in this genomic region.

Example 2

Presented by way of example, but not limitation, FIG. 5 shows a flow chart diagram illustrating a preferred embodiment of the methods of the invention.

Example 3

The Complementary Strand Filtering Method was evaluated for its ability to recognize and filter false positive hybridization signals resulting from cross-hybridization by analyzing the 180,361 bp region of human chromosome 13q14.2 containing the human Retinoblastoma (Rb) gene using the methods of the invention. The genomic organization of the Rb gene has been extensively studied, and it is known that the gene contains 28 exons that are spliced together to generate a 4,561 bp transcript (see, e.g., Toguchida et al., 1993, *Genomics* 17:535–543; Friend et al., 1986, *Nature* 323:643–646).

A tiled genome array was generated in two steps. First, the 180,361 bp region from human chromosome 13 (Genbank Accession Number L11910) was parsed into a list of 180, 300 60-mers for probe selection. This list of possible probes was analyzed by the RepeatMasker computer program, which identified 11,520 of the potential probes as containing regions of low information content (e.g., repetitive elements, simple repeats, or polyX repeats); these 11,520 sequences were eliminated from further analysis. Second, a high-density oligonucleotide array was synthesized containing the remaining sequences tiled in 8 bp steps. Specifically, the array contained 11,022 different 60-mer probes complementary to the genomic region encoding the Rb gene, as well as the reverse complements for each of the different complementary 60-mer probes, so that a total of 22,044 probes, half of the probes being complementary to each strand, were tiled through the entire 180,361 bp region containing the Rb gene.

The array was synthesized on a 1×3 inch glass slide using ink-jet technology developed by Rosetta Inpharmatics (Blanchard, International Patent Publication WO 98/41531, published Sep. 24, 1998).

Target polynucleotides were obtained by preparing total RNA from two cell lines, Jurkat (ATCC #TIB-152) and K562 (ATCC #CCL-243), as described in Example 1. Poly-A+ RNA (mRNA) was isolated from each cell line and labeled using reverse transcription primed with a mixture of random 9-mers and d(T)-20 primers. Specifically, 1.5 µg of mRNA was mixed with 1.0 µg of random 9-mers and 2.5 µg of d(T)-20, and the mixture was incubated for 10 minutes at 70° C., 10 minutes at 4° C., and 10 minutes at 22° C. To this mixture was added 0.5 mM amino-allyl-dUTP (Sigma A-0410), 0.5 mM dNTP, 1×RT buffer, 5 mM $MgCl_2$, 10 mM DTT, and 200 units Superscript (GibcoBRL), bringing the final reverse transcription reaction volume to 100 µl. This reverse transcription reaction was incubated for 10 minutes at 42° C., then the RNA was hydrolyzed by adding 20 µl EDTA+NaOH and incubating at 65° C. for 20 minutes. The reaction was neutralized by adding 20 µl of 1 M Tris-HCl pH 7.6. The resulting amino-allyl labeled single-stranded cDNA was purified using a Microcon-30 (Millipore, Bedford, Mass.). The purified cDNA resulting from the Jurkat cells was coupled to Cy5 dye using a Cy Dye™ kit (Amersham Pharmacia, Piscataway, N.J., #Q15108), while the purified cDNA resulting from the K562 cells was coupled to Cy3 dye in the same manner.

Prior to analysis on the array, the cDNA samples were combined and added to 3 ml of hybridization solution, consisting of 1 M NaCl, 50 mM MES (pH 6.4), 0.50% Sarcosine, and 30% formamide. The combined samples in hybridization solution were then placed in a plastic bag with the array and incubated for 12 hours at 42° C. on a rotisserie to allow the labeled target polynucleotides to hybridize to the array. Following the hybridization step, the array was washed for 20 seconds at room temperature in a beaker containing 50 ml of the hybridization solution, followed by an additional 20 second wash in a low salt buffer (10 mM NaCl, 50 mM MES (pH 6.4), and 0.005% Sarcosine), then scanned using a GMS 418 scanner (Genetic Microsystems). An image of the scanned array is shown in FIG. 8, and the quantitated hybridization data is shown in FIGS. 9–11.

FIGS. 9A and 9B show the degree of detected hybridization (in log intensities) of cDNA from Jurkat cells (known to express the Rb gene) to each of the probes on the genomic scanning array, plotted relative to the base pair location of this region of human chromosome 13. FIG. 9A depicts the log intensity for each of the 60 mer probes complementary to the coding strand in genomic sequence. FIG. 9B depicts the log intensity for each of the reverse complements for each of the different 60 mer probes. Both sets of probes were printed on the same array. Dots along the top of each graph indicate the position along the 180 kb region of genomic DNA where probes were printed (as noted, probes containing regions of low information content were not printed). Small vertical bars along the bottom of each graph indicate the location of the 28 known exons for the Rb gene.

As can be seen in FIGS. 8 and 9A, the raw hybridization data obtained from the Rb scanning array contains a number of probes that hybridize to non-exon regions of the Rb gene sequence. These "false positive" hybridization signal intensities observed in FIGS. 8 and 9A appear to be due to cross hybridization with non-exact complements, particularly those of high abundance in the biological sample being hybridized.

To study the ability of the Complementary Strand Filtering Method previously described in Section 5.2.6 herein to eliminate background signal, the raw data shown in FIGS. 8 and 9A were processed using the difference threshold algorithm as described in step (2)(a) (Section 5.2.6 herein). A rectangular window of total width 9 for each strand was chosen, and the difference threshold d was set equal to 1. The results were then post-processed with a median filter of total width equal to 3. The results are depicted in FIG. 10B.

FIG. 10A depicts the log intensity for each of the 60 mer probes complementary to the coding strand of the genomic region encoding the Rb1 gene prior to application of the Complementary Strand Filtering Method. FIG. 10B depicts the same hybridization data after processing the data using the above-described algorithm in the Complementary Strand Filtering Method. As can be seen in FIG. 10B, the filtered hybridization signal intensities show that application of the Complementary Strand Filtering Method results in the removal of a significant number of false positive hybridization signals from the unfiltered data.

To further show that the Complementary Strand Filtering Method can reproducibly eliminate background signal in hybridization data, three different samples of RNA from Jurkat cells known to express the Rb gene (FIGS. 11A–C) and one sample of RNA from K562 cells in which the Rb gene is not expressed at significant levels (FIG. 11D) were analyzed using the scanning array and methods as described for FIG. 8. The filtering parameters used to process the raw hybridization data are identical to those described for FIG. 10. The results are depicted in FIG. 11.

FIGS. 11A–C depict the log intensity of the hybridization signal for three samples of cDNA derived from RNA from Jurkat cells to each of the 60 mer probes complementary to the coding strand of the genomic region encoding the Rb1 gene after application of the Complementary Strand Filtering Method; FIG. 11B depicts the same data as in FIG. 10B.

FIG. 11D depicts the log intensity of the hybridization signal for a sample of cDNA derived from RNA from K562 cells to each of the 60 mer probes complementary to the coding strand of the genomic region encoding the Rb1 gene after application of the Complementary Strand Filtering Method.

Although the reduction in background shown above is useful, it is preferred to measure quantitatively the effectiveness of the algorithm. Since strong positive signals are a guide for further investigation, contiguous high expression probes were grouped together as one putative exon signal, referred to as a "blip". Table 2 presents a summary of the exon and intron blips identified from the hybridization data obtained for array slide 24008 (FIG. 9A) using the raw hybridization data and hybridization data processed using the Complementary Strand Filtering Method using the difference threshold algorithm with d=1, with either no median filter or with a median filter width equal to four.

TABLE 2

Analysis of Hybridization Data from Array Slide 24008

| Method | Total number blips | Exons covered by blips | Blips over exons | Blips over introns |
|---|---|---|---|---|
| Threshold intensity >0.5 | 367 | 27 | 40 | 333 |
| Threshold intensity >0.8 | 160 | 27 | 33 | 132 |
| Threshold intensity >1.0 | 160 | 27 | 33 | 132 |

TABLE 2-continued

Analysis of Hybridization Data from Array Slide 24008

| Method | Total number blips | Exons covered by blips | Blips over exons | Blips over introns |
|---|---|---|---|---|
| Difference d = 1.0, Total filter width = 9, no median filter | 38 | 24 | 26 | 16 |
| Difference d = 1.0, Total filter width = 9, median filter width = 4 | 28 | 24 | 24 | 7 |

It is well known that the Rb coding sequence consists of 28 exon sequences. The data presented in Table 2 show that the Complementary Strand Filtering Method reduces the number of array probes that give rise to false positive hybridization signals while still maintaining the hybridization signals from array probes that are complementary to the known exon regions of the Rb gene.

Example 4

Scanning array analyses were used to monitor all exons on a particular chromosome under different experimental conditions, and to group exons into genes. For the analysis of chromosome 22q depicted in FIG. 13, a single ink-jet printing-produced oligonucleotide microarray (see U.S. Pat. No. 6,028,189) was designed to represent 8,183 sequences that had been previously identified or confirmed as having coding potential by Dunham, et al., 1999, *Nature* 402:489–95. Two sources of information were used. The first source consisted of 6,650 Genscan-predicted exon sequences, and the second source consisted of 3,381 validated exon sequences identified by aligning the first complete version of the human chromosome 22 sequence with sequences from experimentally validated transcripts, as described in Dunham, et al. From this total set of 10,031 exons, 1,847 exons had coordinates identical to those of other exons and were removed from the sequence pool. The remaining 8,183 exon sequences were subjected to an oligonucleotide design process to identify the two best candidate probes for a given exon sequence, as described below.

For each of the predicted exons, the top two 60-mers were selected using an algorithm that takes into account binding energies, base composition, sequence complexity, cross-hybridization binding energies, and secondary structure (see Friend et al., International Patent Publication WO 01/05935, published Jan. 25, 2001). For exon sequences of 60 nucleotides or less, a single probe was designed consisting of the entire exon sequence. For the 8,183 predicted exons on chromosome 22, 15,511 60-mers were selected and printed on a single array.

For this analysis, exon expression was determined for 69 pairs of conditions, as shown in FIG. 13. The following human cell lines were used: Jurkat (T lymphocyte, ATCC #TIB-152), K562 (chronic myelogenous leukemia, ATCC #CCL-243), Raji (B lymphocytes, ATCC #CCL-86), Colo (colorectal adenocarcinoma, ATCC #CCL-220), 293 (kidney, ATCC #CRL-1573.1) and HepG2 (hepatocellular carcinoma, ATCC #CRL-11997). Poly-A+RNA (mRNA) was isolated from each of the cytoplasmic RNA samples as described above. The "Pool" RNA sample described in FIG. 13 contains an equal mixture of four human cell lines described above (Jurkat, K562, Raji, and Colo). The 41 mRNA samples from the different human tissues described in FIG. 13 were purchased from Clontech and are described in an electronic supplement, available on the Internet at rii.com/Publications.

For a single hybridization, 1.5 µg of mRNA was combined with 1.0 µg of random 9-mers and the mixture was incubated for 10 minutes at 70° C., 5 minutes at 4° C., and 10 minutes at 22° C. To this mixture was added 0.5 mM amino-allyl dUTP (Sigma A-0410), 0.5 mM dNTP, 1×RT buffer, 5 mM $MgCl_2$, 10 mMDTT, and 200 units Superscript (GibcoBRL), bringing the final reverse transcription reaction volume to 400 µl. This reverse transcription reaction was incubated for 20 minutes at 42° C. then the RNA was hydrolyzed by adding 20 µl EDTA+NaOH and incubating at 65° C. for 20 minutes. The reaction was neutralized by adding 20 µl of 1M Tris-HCl pH 7.6. The resulting amino-allyl labeled single-stranded cDNA was purified using a Microcon-30 (Millipore, Bedford, Mass.).

The purified cDNA was coupled to either Cy3 or Cy5 dye using a CyDye™ kit (Amersham Pharmacia, Piscataway, N.J., #Q15108). The dye incorporation and total cDNA were determined spectrophotometrically. Hybridization to the array was carried out as described in Example 1.

Array images were processed to obtain background noise, single channel intensity, and associated measurement error estimates. Expression changes between two samples were quantified as $\log_{10}$ (expression ratio) where the "expression ratio" was taken to be the ratio between normalized, background-corrected intensity values for the two channels (red and green) for each spot on the array. An error model for the log ratio was applied to quantify the significance of expression changes between two samples. The color displays depicted in FIG. 13 show $\log_{10}$ (expression ratio) as red when the red channel is up-regulated relative to the green channel; green when the red channel is down-regulated relative to the green channel; black when the $\log_{10}$ (expression ratio) is close to zero, and grey when data from one or both of the channels for a given probe is unreliable. (As depicted in FIGS. 13A–E, red is generally shown as darker shades of gray, and green is shown as lighter shades of gray.)

A gene identification algorithm was developed that uses intensity and ratio information. Exons were grouped into Expression Verified Genes (EVGs) using a two-step gene identification algorithm. First, each probe was assigned a similarity measure based on taking the moving average (using a window size equal to 6 probes) of pair-wise Pearson correlation coefficients between the log ratios of probe intensities in neighboring exons. Probes with correlation coefficients above 0.5 in a given window were selected as seeds for EVGs. The 0.5 threshold and windows size were determined empirically by training the model on a subset of the known chromosome 22 genes. Second, probes neighboring a seed region were merged into the region if the pair-wise correlation coefficients between the neighboring probe and the average in the seed region exceeded 0.5. This process continued, allowing for gaps between probe pairs to account for failed probes and/or false exon predictions (gaps were not allowed to exceed 5 probes), until no probes flanking the candidate region met the significance threshold of correlation with the exon cluster. The final exon clusters resulting from the gene detection algorithm were identified as an EVG.

Not all condition pairs (rows) were considered in forming EVGs. Elements in a given row had to have significant p-values (equal to or less than the 0.01) to be included in the analysis. Once an EVG was formed, the color display, such as that given in FIG. 13, was updated by reordering the condition pairs according to a hierarchical clustering algorithm.

The resultant 567 groups of co-regulated exons are referred to as EVGs. FIGS. 13B–E show expanded views of specific regions of chromosome 22. These examples demonstrate how expression data can be used to confirm the exons and structure of a known gene (FIG. 13B), to identify potential false positive exon predictions (FIG. 13C), to merge UniGene clusters into a single gene (FIG. 13D), and to experimentally verify ab initio gene predictions (FIG. 14E).

To determine the performance of the chromosome-wide analysis, experimentally derived EVG's were compared to the list of 545 genes annotated by Dunham, et al., 1999, Nature 402:489–95. These annotated genes were divided into four categories (known, related, predicted, and ab initio) based on the level of experimental support for the predictions. Analysis of the expression data from the 69 condition pairs with the gene detection algorithm identified 210 (85%) of the 247 known genes. The remaining 15% of known genes did not exhibit sufficient differential expression regulation among the conditions tested to enable ratio-based algorithms to verify them. The method also detected 66% of the related genes and 53% of the predicted genes. Of 325 ab initio genes that were pure Genscan predictions at the time of the chromosome 22 publication, Dunham et al. speculated that only 100 of these predicted transcripts were expected to represent portions of actual genes. However, found experimental support was found for 185 (57%) of the genes in this category.

In a small number of cases, the EVGs detected contained more than one gene. This occurred when adjacent genes were co-regulated across the 69 experimental conditions tested. In most cases, this situation can be addressed by testing additional conditions or by using additional bioinformatic techniques, such as ORF analysis, identification of internal polyadenylation sites, and supporting EST and protein sequence data. In a few cases, a single gene was represented by multiple EVG's indicating possible alternative spicing.

Example 5

Scanning arrays were designed that covered both strands of various genomic regions on chromosome 22 defined by EVGs where the underlying gene structure was thought to be incomplete. FIG. 14 shows an example of how the scanning approach was used to refine the structure of a novel testis transcript. An ink-jet printing-produced array was fabricated that contained 60 mer probes spaced in 10 base-pair intervals across both strands of a 113 kb BAC clone containing the novel testis gene. The reverse complements for each of the probes were also included on the array to allow transcripts on either strand to be detected. The array was hybridized with mRNA from testis that was fluorescently labeled as described above. The testis-specific mRNA was fluorescently labeled and hybridized to the scanning array as described in Example 1. The resulting probe intensities were analyzed to determine the approximate locations of the exons within this region. For each exon, the hybridization data effectively reduced the search for the intron/exon boundaries down to ~20–30 bp regions. The exact splice junctions were identified using common rules (e.g. GT-AG consensus sequence and ORF analysis). As shown in FIG. 14, the scanning array results extend the 3' UTR by 450 bp and one of the internal coding exons by 102 bases (34 amino acids). In contrast, only 4 of the 6 exons were correctly predicted by Genscan. The results were confirmed by RT-PCR and sequencing. The mRNA (GenBank Accession No. AF324466) derived from this validated and corrected gene is 1,312 nucleotides in length including a 649 base 3'-LTTR with a polyadenylation signal at base 1,293. The mRNA encodes a 217-residue protein and a BLASTP search revealed only one significant match (E-value~$10^{-5}$) to a predicted gene product CG5280 from the Drosophila genome project.

Example 6

Screening arrays were used to survey the entire human genome. Ink-jet oligonucleotide microarrays were designed to a set of 442,785 predicted exons selected from the publicly available assembled sequence in the Ensembl database as of Jun. 15, 2000. Specifically, 554,202 non-redundant sequences were selected from an initial set of 628,635 Genscan predicted exons. An additional 111,417 sequences were removed from the list after being flagged by the RepeatMasker algorithm, which is available by file transfer protocol at ftp.genome.washington.edu/cgi-bin/RepeatMasker.

For each of the predicted exons, the top two 60-mers were selected using an algorithm that takes into account binding energies, base composition, sequence complexity, cross-hybridization binding energies, and secondary structure (see Friend et al., International Patent Publication WO 01/05935, published Jan. 25, 2001). For exon sequences of 60 nucleotides or less, a single probe was designed consisting of the entire exon sequence. For the whole-genome exon arrays, a total of 1,090,408 60 mers were selected to represent the 442,785 Genscan predicted exons from the Ensembl database. For 78,486 of the exons annotated as 'confirmed', the reverse-complement probes were also selected and placed next to the regular probes on the array as negative controls. Labeled cDNA was prepared as described in Example 4.

Fluorescently labeled cDNA from a human lymphoblast cell line and a colorectal carcinoma cell line were hybridized to the arrays, and the resulting fluorescent data analyzed as described in Example 5. Analysis of fluorescence intensities from this single pair of experimental conditions permitted detection of 58% of the 78,486 Ensembl confirmed exons. For the 364,299 predicted exons that did not meet the Ensembl "confirmed" criteria, the fraction detected fell to 34%. The false positive rate for this analysis was estimated to be approximately 5% from an analysis of a set of negative control probes included on the arrays. A summary of the exons validated by this genome survey is given in FIG. 16 and a full listing is provided as a supplement at www.rii.com/Publications.

An intensity-based algorithm was used to experimentally verify predicted exons across the entire human genome. Specifically, raw intensity measurements for forward-strand (FS) probes and the corresponding raw intensity measurements for reverse-complement (RC) probes were used in conjunction with the respective standard deviations of those measurements to determine the significance of the FS probe intensities. RC probes were used to control for non-specific cross hybridization, given that the reverse complement of a DNA sequence has sequence complexity that is equivalent to the forward strand sequence with respect to a variety of measures (e.g., measures such as GC content and GC trend are invariant under the reverse complement). An exon was called present if the intensity difference between an FS probe and the RC probe had a p-value<0.01 in either the red or green channel, and if the FS probe intensity had a p-value<0.01 for being above background in the channel where the difference was considered most significant. P-values were computed using a t-test applied to the difference of the mean pixel intensities and to the difference of the mean FS/background intensities. Single channel exon detection methods were applied only to those exons in which reverse-complement probes were designed. In the remaining cases, the significance of the single channel intensities was determined using the above-background criterion described above.

FIG. 16 shows the percentage of exons detected with the above method. Detection percentages given for the predicted exons listed in FIG. 16 were corrected using an error model described by Hughes, et al., 2000, *Cell* 102:109–126. The corrections were based on false positive estimates for above-background calls that were determined using the FS/RC probe intensity difference calls for the confirmed exons. Of the 88,374 confirmed exons represented on the genome-wide exon arrays, 78,486 had corresponding RC probes. To assess the rate of false positives expected in the single-channel assessments, a similar detection procedure was used to determine the number of RC probe intensity measurements that were significantly greater than the corresponding FS probe intensity. The false positive rate of detection using the single channel method was approximately 5%.

7. References Cited

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

nucleotide sequences, each said different nucleotide sequence comprising a sequence complementary and hybridizable to a different genomic sequence of the same species of organism, said respective genomic sequences for the probes being found at sequential predetermined sites in said genome of said species of organism, said contacting being under conditions conducive to hybridization between said RNAs or nucleic acids derived therefrom and said probes;

(b) identifying the one or more probes to which hybridization of one or more of said RNAs or nucleic acids derived therefrom occurs; and (c) identifying said genomic sequences for each said identified probe as the location of an exon within the genome of said species of organism.

2. The method of claim 1, wherein step (a) is repeated with RNAs or nucleic acids derived therefrom from a plurality of different cells of said species of organism.

3. The method of claim 1, wherein said array has in the range of 150 to 1,000 different polynucleotide probes per 1 cm$^2$.

4. The method of claim 1, wherein said array has in the range of 1,000 to 10,000 different polynucleotide probes per 1 cm$^2$.

5. The method of claim 1, wherein said array has in the range of 10,000 to 50,000 different polynucleotide probes per 1 cm$^2$.

6. The method of claim 1, wherein said array has greater than 50,000 different polynucleotide probes per 1 cm$^2$.

7. The method of claim 1, wherein the nucleotide sequences of the probes consist of up to 1000 nucleotides.

8. The method of claim 1, wherein the probes are 10–200 nucleotides in length.

9. The method of claim 1, wherein the probes are 80–120 nucleotides in length.

10. The method of claim 1, wherein the probes are 40–80 nucleotides in length.

11. The method of claim 1, wherein the nucleotide sequences of the probes consist of 60 nucleotides.

12. The method of claim 1, wherein said genomic sequences for different probes are overlapping in said genome.

What is claimed is:

1. A method of identifying the location of exons within the genome of a species of organism comprising:

(a) contacting a sample comprising RNAs or nucleic acids derived therefrom from one or more cells of said species of organism with an array, said array comprising a positionally-addressable ordered array of polynucleotide probes bound to a solid support, said polynucleotide probes comprising a first plurality of at least 100 polynucleotide probes of different, predetermined 13. The method of claim 1, wherein said genomic sequences for different probes are overlapping in said genome from 10–50% of the length of each said different probe.

14. The method of claim 1, wherein said genomic sequences for different probes are adjacent in said genome.

15. The method of claim 1, wherein said genomic sequence for each probe is spaced apart from that for other probes in said genome by less than 200 bp.

16. The method as in one of claims 7–11, wherein said genomic sequences for different probes are overlapping in said genome.

17. The method as in one of claims 7–11, wherein said genomic sequences for different probes are overlapping in said genome from 10–50% of the length of each said different probe.

18. The method as in one of claims 7–11, wherein said genomic sequences for different probes are adjacent in said genome.

19. The method as in one of claims 7–11, wherein said genomic sequence for each probe is spaced apart from that for other probes in said genome by less than 200 bp.

20. The method of claim 1, wherein said organism is a eukaryote.

21. The method of claim 1, wherein said organism is a human.

22. The method of claim 1, wherein said organism is a plant.

23. The method of claim 1, wherein said organism is a mammal.

24. The method of claim 1, wherein said first plurality of polynucleotide probes is at least 1,000 probes.

25. The method of claim 1, wherein said first plurality of polynucleotide probes is at least 10,000 probes.

26. The method of claim 1, wherein said first plurality of polynucleotide probes is in the range of 1,000 to 50,000 probes.

27. The method of claim 1, wherein two or more of said polynucleotide probes are complementary and hybridizable to intron sequences of at least 10 different genes.

28. The method of claim 1, wherein the distance between 5' ends of said sequential sites is always less than 500 bp, and wherein the genomic sequences for said first plurality of probes span a genomic region of at least 25,000 bp.

29. The method of claim 1, wherein two or more of said polynucleotide probes are complementary and hybridizable to sequences contained entirely within an intron, and herein said ordered array does not comprise a second plurality of polynucleotide probes hat do not comprise a sequence complementary and hybridizable to said genome of said species of organism, said second plurality being of equal or greater number than said first plurality.

30. The method of claim 1, wherein two or more of said polynucleotide probes are complementary and hybridizable to intron sequences of at least 10 different genes, and wherein said ordered array does not comprise a second plurality of polynucleotide probes that do not comprise a sequence complementary and hybridizable to said genome of said species of organism, said second plurality being of equal or greater number than said first plurality.

31. The method of claim 1, wherein:
   (a) said polynucleotide probes further comprise a second plurality of polynucleotide probes comprising a sequence complementary and hybridizable to said first plurality; and
   (b) said identifying step comprises using a hybridization signal generated in said contacting step from said second plurality to filter a hybridization signal generated in said contacting step from said first plurality.

32. The method of claim 1, wherein:
   (a) said sample comprises RNAs or nucleic acids derived therefrom from (i) a first cell or cells of a first tissue type or subject to a first condition, and (ii) a second cell or cells of a second tissue type different from said first tissue type or subject to a second condition different from said first condition; and
   (b) said identifying step comprises comparing a hybridization signal generated in said contacting step from said first cell or cells to a hybridization signal generated in said contacting step from said second cell or cells.

33. The method of claim 1, wherein said plurality of probes is tiled across a sequence predicted to contain, or known to contain, exons.

34. The method of claim 1, wherein said plurality of probes includes known expressed sequence tags (ESTs) or predicted exons.

35. The method of claim 1, wherein each of said plurality of probes is complementary and hybridizable to a predicted or known exon.

36. The method of claim 1, further comprising a sample comprising a population of cellular RNA or nucleic acid derived therefrom on the surface of said solid support such that said sample is in contact with said polynucleotide probes, under conditions conducive to hybridization between said population and said polynucleotide probes.

37. The method of claim 36 wherein said population is labeled.

38. The method of claim 36 wherein said population comprises total cellular mRNA or nucleic acid derived therefrom.

39. The method of claim 36 wherein said population comprises nucleic acids of at least 10,000 different sequences.

40. A computer system for identifying the location of exons within the genome of a species of organism, said computer system comprising:
   one or more processor units; and
   one or more memory units connected to said one or more processor units, said one or more memory units containing one or more programs which cause said one or more processor units to execute steps of:
   (a) receiving a first data structure comprising a first plurality of measured hybridization signals from an array comprising a positionally-addressable ordered array of polynucleotide probes bound to a solid support, said polynucleotide probes comprising a second plurality of at least 100 polynucleotide probes of different, predetermined nucleotide sequences, each said different nucleotide sequence comprising a sequence complementary and hybridizable to a different genomic sequence of the same species of organism, said respective genomic sequences for the probes being found at sequential predetermined sites in said genome of said species of organism, said array contacting a sample comprising RNAs or nucleic acids derived therefrom from one or more cells of said species of organism with said array, said contacting being under conditions conducive to hybridization between said RNAs or nucleic acids derived therefrom and said probes;
   (b) receiving a second data structure comprising the nucleotide sequence of said genome of said organism;
   (c) receiving a third data structure comprising the nucleotide sequence of said second plurality of polynucleotide probes, said third data structure identifying the positional location of each said probe on said array;
   (d) identifying the one or more probes to which hybridization of one or more of said RNAs or nucleic acids derived therefrom occurs;
   (e) identifying said genomic sequences for each said identified probe as the location of an exon within the genome of said species of organism; and (f) outputting the locations of said exons with respect to the nucleotide sequence of said genome of said organism.

41. A computer program product for identifying the location of exons within the genome of a species of organism, the computer program product for use in conjunction with a computer having a memory and a processor, the computer program product comprising a computer readable storage medium having a computer program mechanism encoded thereon, wherein said computer program mechanism can be loaded into the one or more memory units of a computer and cause the one or more processor units of the computer to execute the steps of:

(a) receiving a first data structure comprising a first plurality of measured hybridization signals from an array comprising a positionally-addressable ordered array of polynucleotide probes bound to a solid support, said polynucleotide probes comprising a second plurality of at least 100 polynucleotide probes of different, predetermined nucleotide sequences, each said different nucleotide sequence comprising a sequence complementary and hybridizable to a different genomic sequence of the same species of organism, said respective genomic sequences for the probes being found at sequential predetermined sites in said genome of said species of organism, said array contacting a sample comprising RNAs or nucleic acids derived therefrom from one or more cells of said species of organism with said array, said contacting being under conditions conducive to hybridization between said RNAs or nucleic acids derived therefrom and said probes;

(b) receiving a second data structure comprising the nucleotide sequence of said genome of said organism;

(c) receiving a third data structure comprising the nucleotide sequence of said second plurality of polynucleotide probes, said third data structure identifying the positional location of each said probe on said array;

(d) identifying the one or more probes to which hybridization of one or more of said RNAs or nucleic acids derived therefrom occurs;

(e) identifying said genomic sequences for each said identified probe as the location of an exon within the genome of said species of organism; and (f) outputting the locations of exon boundaries with respect to the nucleotide sequence of said genome of said organism.

* * * * *